US008236756B2

(12) United States Patent
Balzarini et al.

(10) Patent No.: US 8,236,756 B2
(45) Date of Patent: Aug. 7, 2012

(54) PRODRUGS CLEAVABLE BY CD26

(75) Inventors: Jan Balzarini, Heverlee (BE); Maria José Camarasa Ríus, Getafe (ES); Sonsoles Velázquez Díaz, Soto del Real (ES)

(73) Assignees: Consejo Superior de Investigaciones Cientificas (CSIC), Madrid (ES); K.U. Leuven Research & Development, Leuven (BE)

( * ) Notice: Subject to any disclaimer, the term of this patent is extended or adjusted under 35 U.S.C. 154(b) by 439 days.

(21) Appl. No.: 10/555,930

(22) PCT Filed: May 10, 2004

(86) PCT No.: PCT/BE2004/000069
§ 371 (c)(1),
(2), (4) Date: Jul. 31, 2007

(87) PCT Pub. No.: WO2004/098644
PCT Pub. Date: Nov. 18, 2004

(65) Prior Publication Data
US 2007/0275900 A1    Nov. 29, 2007

(30) Foreign Application Priority Data

May 8, 2003   (GB) .................................. 0310593.9

(51) Int. Cl.
*A61K 47/48* (2006.01)
*C07D 473/00* (2006.01)
*C07H 15/252* (2006.01)

(52) U.S. Cl. ...... 514/3.7; 514/3.8; 514/21.9; 514/21.91; 514/34; 514/49; 514/50; 514/263.38

(58) Field of Classification Search .................. None
See application file for complete search history.

(56) References Cited

U.S. PATENT DOCUMENTS

| 4,256,632 | A | * | 3/1981 | Levin et al. | .................. | 530/322 |
| 4,892,939 | A | * | 1/1990 | Sakai et al. | ..................... | 514/50 |
| 5,627,035 | A | * | 5/1997 | Vahlne et al. | ................. | 435/7.2 |
| 5,783,689 | A | * | 7/1998 | Miller et al. | .............. | 536/28.52 |
| 5,939,550 | A | * | 8/1999 | Braish et al. | ................. | 546/123 |
| 5,962,216 | A |   | 10/1999 | Baurain et al. | | |

(Continued)

FOREIGN PATENT DOCUMENTS
WO    WO 97/45117 A1    12/1997

(Continued)

OTHER PUBLICATIONS

Anand et al., "Novel Dipeptide Prodrugs of Acyclovir for Ocular Herpes Infections: *Bioreversion, Antiviral Activity and Transport Across Rabbit Cornea*," Curr. Eye Res. 26:151-163 (2003).

(Continued)

Primary Examiner — Jeffrey E Russel
(74) Attorney, Agent, or Firm — Clark & Elbing LLP

(57) ABSTRACT

The present invention provides a new prodrug technology and new prodrugs in order to increase the solubility, to modulate plasma protein binding or to enhance the bioavailability of a drug. In the present invention the prodrugs are conjugates of a therapeutic compound and a peptide (eg tetrapeptide or hexapeptide) wherein the conjugate is cleavable by dipeptidyl-peptidases, more preferably by CD26, also known as DPPIV (dipeptidyl aminodipeptidase IV). The present invention furthermore provides a method of producing the prodrugs, to enhance brain and lymphatic delivery of drugs and/or to extend drug half-lives in plasma.

17 Claims, 9 Drawing Sheets

U.S. PATENT DOCUMENTS

| | | | |
|---|---|---|---|
| 6,177,404 B1* | 1/2001 | DeFeo-Jones et al. | 514/8 |
| 6,699,871 B2* | 3/2004 | Edmondson et al. | 514/249 |
| 2002/0142955 A1* | 10/2002 | Dubois et al. | 514/12 |
| 2003/0139353 A1 | 7/2003 | Jackson et al. | 514/27 |
| 2004/0121969 A1* | 6/2004 | Hendricks et al. | 514/43 |
| 2004/0180893 A1* | 9/2004 | Balzarini et al. | 514/237.8 |
| 2005/0054678 A1* | 3/2005 | Yasuda et al. | 514/326 |

FOREIGN PATENT DOCUMENTS

| | | |
|---|---|---|
| WO | WO 99/67278 A1 | 12/1999 |
| WO | WO 00/71571 A2 | 11/2000 |
| WO | WO 03/048190 A2 | 6/2003 |

OTHER PUBLICATIONS

Augustyns et al., "The Unique Properties of Dipeptidyl-Peptidase IV (DPP IV / CD26) and the Therapeutic Potential of DPP IV Inhibitors," *Curt Med. Chem.* 6:311-327 (1999).

Balajthy et al., "Synthesis and Functional Evaluation of a Peptide Derivative of 1-β-D-Arabinofuranosylcytosine," *J. Med. Chem.* 35:3344-3349 (1992).

De Meester et al., "CD26, Let it Cut or Cut it Down," *Rev. Immunol. Today* 20:367-375 (1999).

Masquelier et al., "Amino Acid and Dipeptide Derivatives of Daunorubicin: *1. Synthesis, Physicochemical Properties, and Lysosomal Digestion,*" *J. Med. Chem.* 23:1166-1170 (1980).

Trouet et al., "Extracellularly Tumor-Activated Prodrugs for the Selective Chemotherapy of Cancer: *Application to Doxorubicin and Preliminary in Vitro and in Vivo Studies,*" *Cancer Res.* 61:2843-2846 (2001).

Yaron et al., "Proline-Dependent Structural and Biological Properties of Peptides and Proteins," *Crit. Rev. Biochem. Mol. Biol.* 28:31-81 (1993).

International Search Report (PCT/BE2004/000069) (mailed Sep. 30, 2004).

Written Opinion of International Searching Authority (PCT/BE2004/000069) (mailed Sep. 30, 2004).

International Preliminary Report on Patentability (PCT/BE2004/000069) (mailed Sep. 29, 2005).

Anand et al., "Novel dipeptide prodrugs of acyclovir for ocular herpes infections: Bioreversion, antiviral activity and transport across rabbit cornea," *Current Eye Research* 26(3-4):151-163, 2003.

Durinx et al., "Molecular characterization of dipeptidyl peptidase activity in serum: soluble CD26/dipeptidyl peptidase IV is responsible for the release of X-Pro dipeptides," *European Journal of Biochemistry* 267(17):5608-5613, 2000.

Hinke et al., "Metformin effects on dipeptidylpeptidase IV degradation of glucagon-like peptide-1," *Biochemical and Biophysical Research Communications* 15:291(5):1302-1308, 2002.

Iwaki-Egawa et al., "Dipeptidyl peptidase IV from human serum: purification, characterization, and N-terminal amino acid sequence," *Journal of Biochemistry* 124(2):428-433, 1998.

Kieffer et al., "Degradation of glucose-dependent insulinotropic polypeptide and truncated glucagon-like peptide 1 in vitro and in vivo by dipeptidyl peptidase IV," *Endocrinology* 136(8):3585-3596, 1995.

Smal et al. "Activation and cytotoxicity of 2-alpha-aminoacyl prodrugs of methotrexate," *Biochemical Pharmacology* 49(4):567-574, 1995.

Office Action for Japanese Patent Application No. 504046/2006, mailed Mar. 30, 2010. English translation provided.

Official Communication for European Patent Application EP-A-1 620 130 (04731856.3), dated Apr. 29, 2010.

Official Communication for Canadian Patent Application No. 2,525,191, dated Jan. 27, 2011.

Official Communication for Japanese Patent Application No. 504046/2006, mailed Feb. 8, 2011. English translation provided.

Official Communication for Canadian Patent Application No. 2,525,191, dated Feb. 27, 2012.

\* cited by examiner

NAP-TSAO-T
(CAM-212)

Val-NAP-TSAO-T
(CAM-403)

Val-Pro-NAP-TSAO-T
(CAM-405)

Val-Pro-Val-NAP-TSAO-T
(CAM-431)

CH$_3$-Val-Pro-Val-NAP-TSAO-T
(CAM-407)

Z-Val-Pro-Val-Pro-OtBu (X)   [SEQ ID NO: 6]

Z-Val-Pro-Val-Pro-OtBu (Y)   [SEQ ID NO: 6]

Z-Val-Pro-6-aminoquinoline (H)

H-Val-Pro-6-aminoquinoline (I)

Boc-Val-Pro-Ara-C (A)

HCl. H-Val-Pro-Ara-C (B)

Z-Val-Pro-Val-Pro-Ara-C (D)

SEQ ID NO: 9

H-Val-Pro-Val-Pro-Ara-C (E)

SEQ ID NO: 6

Fmoc-Val-Pro-doxorubicin (F)

H-Val-Pro-doxorubicin (G)

SEQUENCE LISTING

```
<160> NUMBER OF SEQ ID NOS: 12

<210> SEQ ID NO 1
<211> LENGTH: 4
<212> TYPE: PRT
<213> ORGANISM: Artificial Sequence
<220> FEATURE:
<223> OTHER INFORMATION: prodrug peptide component

<400> SEQUENCE: 1

Arg Pro Lys Pro
1

<210> SEQ ID NO 2
<211> LENGTH: 5
<212> TYPE: PRT
<213> ORGANISM: Artificial Sequence
<220> FEATURE:
<223> OTHER INFORMATION: prodrug peptide component

<400> SEQUENCE: 2

Val Pro Asp Pro Arg
1               5

<210> SEQ ID NO 3
<211> LENGTH: 4
<212> TYPE: PRT
<213> ORGANISM: Artificial Sequence
<220> FEATURE:
<223> OTHER INFORMATION: prodrug peptide component

<400> SEQUENCE: 3

Gly Pro Tyr Pro
1

<210> SEQ ID NO 4
<211> LENGTH: 6
<212> TYPE: PRT
<213> ORGANISM: Artificial Sequence
<220> FEATURE:
<223> OTHER INFORMATION: prodrug peptide component

<400> SEQUENCE: 4

Gly Pro Tyr Pro Tyr Pro
1               5

<210> SEQ ID NO 5
<211> LENGTH: 4
<212> TYPE: PRT
<213> ORGANISM: Artificial Sequence
<220> FEATURE:
<223> OTHER INFORMATION: CD26 substrate

<400> SEQUENCE: 5

Asp Pro Lys Pro
1

<210> SEQ ID NO 6
<211> LENGTH: 4
<212> TYPE: PRT
<213> ORGANISM: Artificial Sequence
<220> FEATURE:
<223> OTHER INFORMATION: prodrug peptide component

<400> SEQUENCE: 6

Val Pro Val Pro
```

-continued

```
<210> SEQ ID NO 7
<211> LENGTH: 4
<212> TYPE: PRT
<213> ORGANISM: Artificial Sequence
<220> FEATURE:
<223> OTHER INFORMATION: prodrug peptide component

<400> SEQUENCE: 7

Val Ala Val Pro
1

<210> SEQ ID NO 8
<211> LENGTH: 4
<212> TYPE: PRT
<213> ORGANISM: Artificial Sequence
<220> FEATURE:
<223> OTHER INFORMATION: prodrug peptide component

<400> SEQUENCE: 8

Lys Pro Asp Pro
1

<210> SEQ ID NO 9
<211> LENGTH: 4
<212> TYPE: PRT
<213> ORGANISM: Artificial  Sequence
<220> FEATURE:
<223> OTHER INFORMATION: prodrug peptide component
<220> FEATURE:
<221> NAME/KEY: MOD_RES
<222> LOCATION: (1)..(1)
<223> OTHER INFORMATION: z protection group

<400> SEQUENCE: 9

Val Pro Val Pro
1

<210> SEQ ID NO 10
<211> LENGTH: 4
<212> TYPE: PRT
<213> ORGANISM: Artificial Sequence
<220> FEATURE:
<223> OTHER INFORMATION: prodrug peptide component

<400> SEQUENCE: 10

Val Pro Lys Pro
1

<210> SEQ ID NO 11
<211> LENGTH: 4
<212> TYPE: PRT
<213> ORGANISM: Artificial Sequence
<220> FEATURE:
<223> OTHER INFORMATION: prodrug peptide component

<400> SEQUENCE: 11

Val Pro Asp Pro
1

<210> SEQ ID NO 12
<211> LENGTH: 4
<212> TYPE: PRT
<213> ORGANISM: Artificial Sequence
<220> FEATURE:
<223> OTHER INFORMATION: prodrug peptide component
```

```
<400> SEQUENCE: 12

Gly Pro Phe Pro
1
```

PRODRUGS CLEAVABLE BY CD26

CROSS-REFERENCE TO RELATED APPLICATIONS

This application is the U.S. National Stage of International Application No. PCT/BE2004/000069, filed May 10, 2004, which, in turn, claims the benefit of GB Application No. 0310593.9, filed May 8, 2003.

FIELD OF THE INVENTION

The invention relates to prodrugs of therapeutic compounds which are released or activated by proteolysis of a peptidic moiety. The invention also relates to methods for increasing oral uptake, modify serum protein binding, blood-brain barrier penetration or solubility and bioavailibity of therapeutic compounds.

BACKGROUND OF THE INVENTION

Modern drug discovery techniques (e.g. combinatorial chemistry, high-throughput pharmacological screening, structure-based drug design) are providing very specific and potent drug molecules. However, it is rather common that these novel chemical structures have unfavorable physico-chemical and biopharmaceutical properties. Besides, during the development of new therapeutic agents, researchers typically focus on pharmacological and/or biological properties, with less concern for physicochemical properties. However, the physicochemical properties (dissociation constant, solubility, partition coefficient, stability) of a drug molecule have a significant effect on its pharmaceutical and biopharmaceutical behavior. Thus, the physicochemical properties need to be determined and modified, if needed, during drug development. Moreover, the physicochemical properties of many existing drug molecules already on the market are not optimal.

Today, drug candidates are often discontinued due to issues of poor water solubility or inadequate absorption, leaving countless medical advances unrealized. Still other products make it to the market, but never realize their full commercial potential due to safety or efficacy concerns. Prodrugs have the potential to overcome both challenges. The technology exploits endogenous enzymes for selective bioconversion of the prodrug to the active form of the drug. This technology has the ability to keep promising new drug candidates alive through development, and improving the safety and efficacy of existing drug products.

Prodrugs are mostly inactive derivatives of a drug molecule that require a chemical or enzymatic biotransformation in order to release the active parent drug in the body. Prodrugs are designed to overcome an undesirable property of a drug. As such this technology can be applied to improve the physicochemical, biopharmaceutical and/or pharmacokinetical properties of various drugs. Usually, the prodrug as such is biologically inactive. Therefore, prodrugs need to be efficiently converted to the parent drugs to reach pronounced efficacy as soon as the drug target has been reached.

In general, prodrugs are designed to improve the penetration of a drug across biological membranes in order to obtain improved drug absorption, to prolong duration of action of a drug (slow release of the parent drug from a prodrug, decreased first-pass metabolism of the drug), to target the drug action (e.g. brain or tumor targeting), to improve aqueous solubility and stability of a drug (i. v. preparations, eye-drops, etc.), to improve topical drug delivery (e.g. dermal and ocular drug delivery), to improve the chemical/enzymatic stability of a drug (e.g. peptides) or to decrease drug side-effects.

Many prodrug technologies have already been developed depending on the kind of drug that has to be converted. These prodrug technologies include cyclic prodrug chemistry for peptides and peptidomimetics, phosphonooxymethyl (POM) chemistry for the solubilization of tertiary amines, phenols and hindered alcohols and esterification in general. Also targeting strategies are pursued by coupling groups cleavable by specific enzymes such as the peptide deformylase of bacteria which cleaves N-terminal formyl groups of the peptides or PSA (prostate specific antigen) used to target prostate cancer.

Coupling of peptides or amino acids to a therapeutic agent has already been pursued in the past for several reasons. In the antisense-antigene field, oligonucleotides or intercalators have been conjugated to peptides in order to increase the cellular uptake of the therapeutic agents. These oligonucleotides and intercalators have not to be released after cell penetration however, and can not be regarded as prodrugs. An example of amino acid coupling to a therapeutic compound is Valgancyclovir, the L-valyl ester prodrug of gancyclovir, which is used for the prevention and treatment of cytomegalovirus infections. After oral administration, the prodrug is rapidly converted to gancyclovir by intestinal and hepatic esterases. Recently, alanine and iysine prodrugs of novel anti-tumor benzothiazoles have been investigated [Hutchinson et al. (2002) J. Med. Chem. 45, 744-474].

Peptide carrier-mediated membrane transport of amino acid ester prodrugs of nucleoside analogues has already been demonstrated [Han et al. *Pharm. Res.* (1998) 15: 1154-1159; Han et al *Pharm. Res.* (1998) 15: 1382-1386]. It has indeed been shown that oral bioavailability of drugs can be mediated by amino acid prodrug derivatives containing an amino acid, preferably in the L-configuration. L-Valine seems to have the optimal combination of chain length and branching at the β-carbon of the amino acid for intestinal absorption. hPEPT-1 has been found to be implicated as the primary absorption pathway of increased systemic delivery of L-valine ester prodrugs. Recently, it was shown that the hPEPT-1 transporter need to optimally interact with a free $NH_2$, a carbonyl group and a lipophilic entity, and may form a few additional H-bridges with its target molecule. L-Valine-linked nucleoside analogue esters may fulfill these requirements for efficient hPEPT-1 substrate activity [Friedrichsen et al. Eur. J. Pharm. Sci. (2002) 16: 1-13]. The prior art for ameliorating solubility and bioavailability reveals however only amino acid prodrugs (only one amino acid coupled) of small organic molecules whereby the amino acid is mostly coupled through ester bonds, since they are easily converted back to the free therapeutic agent by esterases.

Prior art documents describe processing of prodrugs by a number of proteases, such as aminopeptidases (PCT application WO01/68145) and aminotripeptidase (PCT application WO02/00263).

There is however still a need for new, alternative and better prodrug technologies and this need is projected to grow, as combinatorial chemistry and high throughput screening continue to produce vast numbers of new compounds with a high molecular weight, high log P [partition coefficient], or poor water solubility.

SUMMARY OF THE INVENTION

The invention provides a novel prodrug technology that can be applied to ameliorate the solubility and/or the bioavailability of therapeutic agents. The invention comprises the derivatisation of (therapeutic or diagnostic) agents in order to ameliorate their solubility and bioavailability. The invention provides conjugates of therapeutic agents with a peptidic moiety wherein said conjugate is cleavable by a dipeptidyl-peptidase, such as CD26. This technology can furthermore be used to modulate the protein binding of a therapeutic compound D and to target specific sites in a mammal.

The present invention provides a new prodrug technology and new prodrugs in order to modulate the solubility, protein binding and/or the bioavailability of a drug. In the present invention the prodrugs are conjugates of a therapeutic compound D and a peptide wherein the conjugate is cleavable by dipeptidyl-peptidases, more preferably by dipeptidyl-peptidase IV. The present invention furthermore provides a method of producing said prodrugs. The invention also provides a prodrug technology to more selectively target drugs, to modify, particularly enhance brain and lymphatic delivery of drugs and/or to extend drug half-lives in plasma.

In one aspect the invention relates to a pharmaceutical composition comprising a prodrug of a therapeutic compound D. The therapeutic compound D is not a peptide or a protein, and the therapeutic compound D includes an amino group, more particularly a terminal primary or secondary amino group, capable of binding with the carboxylgroup of an amino acid. Or alternatively, the therapeutic compound D is bound to a linker comprising an amino group, more in particular a primary or secondary amino group, capable of binding with the carboxylgroup of an amino acid. In a particular embodiment, the therapeutic compound D is also not an oligonucleotide or a nucleic acid intercalating agent. The prodrug is characterised in that said prodrug comprises said therapeutic compound D linked to an oligopeptide, said oligopeptide consisting of a general structure H—[X—Y]$_n$, wherein X is an amino acid (in one embodiment an L-amino acid), wherein n is between 1 and 5 (thereby selected from 1, 2, 3, 4 or 5), wherein Y is an amino acid (in one embodiment an L-amino acid) selected from the group consisting of proline, alanine, hydroxyproline, dihydroxyproline, thiazolidinecarboxylic acid (thioproline), dehydroproline, pipecolic acid (L-homoproline), azetidinecarboxylic acid, aziridinecarboxylic acid, glycine, serine, valine, leucine, isoleucine and threonine, and wherein the binding between the carboxy terminus of H—[X—Y]$_n$ and the amino group of D or its linker occur via an amide. The H—[X—Y]$_n$ peptide has a free aminoterminus, i.e an unmodified NH$_2$ group. For clarity, each X and Y in each repeat unit [X—Y] are chosen independently from one another and independently for each repeat unit. In one embodiment the peptide has between two to five CD26 cleavable repeats. In another embodiment, the number m of amino acids in the linker A$_m$ between the CD26 cleavable oligopeptide and the D is between 1 and 15. More particularly the m is 1. More particularly m is 1 and A is valine. In another embodiment the CD26 cleavable oligopeptide [X—Y]$_n$ is a tetrapeptide or hexapeptide wherein at least one X is an hydrophobic or aromatic amino acid or alternatively, wherein at least one X is an neutral or acidic amino acid, or alternatively, wherein at least one X is a basic amino acid. In a particular embodiment the oligopeptide [X—Y]$_n$ is a tetrapeptide or hexapeptide selected from the group of Val-Y—[X—Y]$_{1-2}$, more in particular Val-Pro-[X—Y]$_{1-2}$ in order to have a good intestinal absorption, followed by a slow or fast release of the therapeutic compound combined with modifications of solubility, depending on the choice of X and Y. In one embodiment the tetra or hexapeptide has a general structure Val-[X—Y] or Val-Y—[X—Y]$_2$ According to one embodiment Y is proline or hydroxyproline or dihydroxyproline or alanine. According to another embodiment, X is selected from Valine, Aspartic acid, Serine, Lysine, Arginine, Histidine, Phenylalanine, Isoleucine or Leucine. According to another embodiment, X is selected from the acidic amino acids Aspartic acid or Glutamic acid in order to have a slow cleavage, from the positively charged amino acids Arginine, Histidine or Lysine in order to have a fast release of the therapeutic compound D. The oligopeptide [X—Y]$_n$ may be coupled via an amide binding to an amino group residing on an organic molecule/atom such as an aromatic group of a therapeutic compound, residing on a carbohydrate or residing on a nucleoside or on a heterocyclic group or residing on an alkyl, alkenyl or alkynyl or residing on an anorganic molecule/atom. In one embodiment the oligopeptide [X—Y]$_n$ is coupled via an amide binding to an amino group residing on an aromatic group of a therapeutic compound, residing on a carbohydrate or residing on a nucleoside. Alternatively, the oligopeptide [X—Y]$_n$ is indirectly coupled to the therapeutic compound D via a linker comprising an amino group. Such a linker can have the general structure of an oligopeptide A$_m$ wherein m ranges between 1 to 15 and more particularly between 1 to 3, or m=1. A in the structure A$_m$ can any amino acid. According to one embodiment m=1 and A is valine. A produg which such a linker has a general structure H—[X—Y]$_n$-A$_m$-D. The oligopeptide A$_m$ or the amino acid A is linked at its aminoterminus via an amide binding to the oligopeptide H—[X—Y]$_n$. The oligopeptide A$_m$ or the amino acid A is linked at its carboxy terminus via an amide or ester binding to the therapeutic compound D. Pharmaceutical compositions can comprise prodrugs of therapeutic compounds for the prevention or treatment of a disorder selected from the group of a bacterial, protozoan, fungal, yeast and viral infections, inflammation, allergy, cancer, depression, pain, neurological-disorders, metabolic disorders, respiratory disorders, urologic disorders, cardiovascular disorders, a disorder of the CNS, immunologic disorders and metabolic diseases. In an embodiment, the pharmaceutical composition comprises prodrugs of compounds for the prevention or treatment of a disorder selected from the group above, other than cancer and/or disorders due to elevated levels of glucose such as obesity and diabetes. A particular example of an antiviral drug is TSAO. Another particular example of an antiviral drug is a HIV protease inhibitor such as described herein. In a particular embodiment, the amino acids selected for X are L-amino acids. In another embodiment the amino acids selected for Y are L-amino acids or for X and Y are L-amino acids. Another embodiment specifically excludes the use of D-amino acids for X and Y. In a particular embodiment, the peptide of the prodrug comprises B$_p$—[X—Y]$_n$-A$_m$ wherein B can be any amino acid or peptide which is cleaved by a peptidase/aminopeptidase and wherein p ranges from 1 to 10 amino acids.

In another aspect, the invention relates to a prodrug construct of a therapeutic compound D, wherein said therapeutic compound D is not an amino acid, a peptide or a protein, and wherein the therapeutic compound D includes a terminal primary or secondary amino group capable of binding with the carboxylgroup of an amino acid or wherein the therapeutic compound D is bound to a linker comprising a primary or secondary amino group capable of binding with the carboxylgroup of an amino acid, said prodrug consisting of said therapeutic compound D linked to an oligopeptide with a general structure H—[X—Y]$_n$, and is characterized in that n=2-5, wherein X is an amino acid (in one embodiment X is an L-amino acid), wherein Y is an amino acid (in one embodiment Y is an L-amino acid) selected from the group consisting of proline, alanine, hydroxyproline, dihydroxyproline, thiazolidinecarboxylic acid (thioproline), dehydroproline, pipecolic acid (L-homoproline), azetidinecarboxylic acid, aziridinecarboxylic acid, glycine, serine, valine, leucine, isoleucine and threonine, and wherein the binding between the carboxy terminus of H—[X—Y]$_n$ and the amino group of D occurs via an amide. In a particular embodiment, the amino acids selected for X are L-amino acids. In another embodiment the amino acids selected for Y are L-amino acids or for X and Y are L-amino acids. Another embodiment specifically excludes the use of D-amino acids for X and Y.

According to one embodiment, this prodrug, upon activation, has no inhibitory effect on the CD26/DPPIV enzyme. In one embodiment n is selected from 2, 3, 4 or 5, yet more particularly the oligopeptide [X—Y]$_n$ is a tetrapeptide or hexapeptide wherein at least one X is a hydrophobic or aromatic amino acid, alternatively wherein at least one X is a neutral or acidic amino acid or, alternatively, wherein at least one X is a basic amino acid. In a particular embodiment the oligopeptide [X—Y]$_n$ is selected from the group of Val-Pro, Asp-Pro, Ser-Pro, Lys-Pro, Arg-Pro, His-Pro, Phe-Pro, lie-Pro, Leu-Pro, Val-Ala, Asp-Ala, Ser-Ala, Lys-Ala, Arg-Ala, His-Ala, Phe-Ala, Ile-Ala and Leu-Ala. According to one embodiment, Y is proline or hydroxyproline or dihydroxyproline or alanine. According to one embodiment, the oligopeptide [X—Y]$_n$ is coupled via an amide binding to an amino group residing on a aromatic group of a therapeutic compound, residing on a carbohydrate or residing on a nucleoside. Alternatively, the oligopeptide [X—Y]$_n$ is indirectly coupled to the therapeutic compound D via a linker comprising an amino group. This linker comprises an organic molecule (i.e. alkylamino, a peptide, or a combination of both). In an embodiment, the number m of amino acids in the linker between the CD26 cleavable oligopeptide and the therapeutic compound D is between 1 and 15. In a particular embodiment, such a linker can have the general structure of an oligopeptide A$_m$ wherein m ranges between 1 to 15 and more particularly between 1 to 3, or m=1. A in the structure A$_m$ can be any amino acid. According to one embodiment m=1 and A is valine. A prodrug with such a linker has a general structure H—[X—Y]$_n$-A$_m$-D. According to one embodiment, the prodrug is a prodrug of a therapeutic compound for the prevention or treatment of a disorder selected from the group of a viral, bacterial, protozoan, fungal, yeast and viral infection, inflammation, allergy, depression, pain, neurological disorders, metabolic disorders, respiratory disorders, urologic disorders, cardiovascular disorders, a disorder of the CNS, immunologic disorders and metabolic diseases other than disorders due to elevated levels of glucose such as obesity and diabetes. According to one embodiment the prodrug is an antiviral drug such as TSAO or NAP-TSAO. According to another embodiment the prodrug is a HIV protease inhibitor prodrug with a general structure of formula (I).

In another aspect the invention relates to a method for modulating (increasing or decreasing) the water solubility, and/or plasma protein binding and/or the bioavailability of a therapeutic compound D by coupling a peptide to said therapeutic compound whereby the resulting conjugate is cleavable by a dipeptidyl-peptidase. According to one embodiment the dipeptidyl peptidase is CD26 and the therapeutic compound D is not a peptide or a protein, and the therapeutic compound D includes a terminal primary or secondary amino group capable of binding with the carboxylgroup of an amino acid or the therapeutic compound D is bound to a linker comprising a primary or secondary amino group capable of binding with the carboxylgroup of an amino acid, and wherein the oligopeptide consists of a general structure H—[X—Y]$_n$, wherein X is an amino acid, wherein n is between 1 and 5, wherein Y is an amino acid selected from the group consisting of proline, alanine, hydroxyproline, dihydroxyproline, thiazolidinecarboxylic acid (thioproline), dehydroproline, pipecolic acid (L-homoproline), azetidinecarboxylic acid, aziridinecarboxylic acid, glycine, serine, valine, leucine, isoleucine and threonine, and wherein the binding between the carboxy terminus of H—[X—Y]$_n$ and the amino group of D occurs via an amide. According to one embodiment, the oligopeptide [X—Y]n is a tetrapeptide or hexapeptide wherein at least one X is a hydrophobic or aromatic amino acid, alternatively wherein at least one X is a neutral or acidic amino acid or, alternatively, wherein at least one X is a basic amino acid. According to one embodiment, the therapeutic compound of which the solubility, plasma protein binding or bioavailability is modified is a therapeutic compound for the prevention or treatment of a disorder selected from the group of a viral, bacterial, protozoan, fungal, yeast and viral infection, inflammation, cancer, allergy, depression, pain, neurological disorders, metabolic disorders, respiratory disorders, urologic disorders, cardiovascular disorders, a disorder of the CNS, immunologic disorders and metabolic diseases. In a particular embodiment, the disorder are other than cancer or disorders due to elevated levels of glucose such as obesity and diabetes. In a particular embodiment, the amino acids selected for X are L-amino acids. In another embodiment the amino acids selected for Y are L-amino acids or for X and Y are L-amino acids. Another embodiment specifically excludes the use of D-amino acids for X and Y.

Another aspect of the invention relates to a method of producing a prodrug, wherein the prodrug is cleavable by a dipeptidyl-peptidase, the method comprising the step of linking a therapeutical active drug D and a peptide with structure H—[X—Y]$_n$ whereby the resulting conjugate is cleavable by CD26. According to one embodiment the dipeptidyl peptidase is CD26 and the therapeutic compound D is not a peptide or a protein, and the therapeutic compound D includes a terminal primary or secondary amino group capable of binding with the carboxylgroup of an amino acid or the therapeutic compound D is bound to a linker comprising a primary or secondary amino group capable of binding with the carboxylgroup of an amino acid, and wherein the oligopeptide consists of a general structure H—[X—Y]$_n$, wherein X is an amino acid, wherein n is between 1 and 5, wherein Y is an amino acid selected from the group consisting of proline, alanine, hydroxyproline, dihydroxyproline, thiazolidinecarboxylic acid (thioproline), dehydroproline, pipecolic acid (L-homoproline), azetidinecarboxylic acid, aziridinecarboxylic acid, glycine, serine, valine, leucine, isoleucine and threonine, and wherein the binding between the carboxy terminus of H—[X—Y]$_n$ and the amino group of D occurs via an amide. According to one embodiment, the oligopeptide [X—Y]$_n$ is a tetrapeptide or hexapeptide wherein at least one X is a hydrophobic or aromatic amino acid, alternatively wherein at least one X is a neutral or acidic amino acid or, alternatively, wherein at least one X is a basic amino acid. In a particular embodiment, the amino acids selected for X are L-amino acids. In another embodiment the amino acids selected for Y are L-amino acids or for X and Y are L-amino acids. Another embodiment specifically excludes the use of D-amino acids for X and Y.

Another aspect of the invention relates to a method of selecting potential prodrugs, said method comprising contacting amino acid prodrugs with dipeptidyl-peptidases or tissue or cells producing dipeptidyl-peptidases and with dipeptidyl-peptidases free medium in a parallel experiment. According to one embodiment the dipeptidyl peptidase is CD26 and the therapeutic compound D is not a peptide or a protein, and the therapeutic compound D includes a terminal primary or secondary amino group capable of binding with the carboxylgroup of an amino acid or the therapeutic compound D is bound to a linker comprising a primary or secondary amino group capable of binding with the carboxylgroup of an amino acid, and wherein the oligopeptide consists of a general structure H—[X—Y]$_n$, wherein X is an amino acid, wherein n is between 1 and 5, wherein Y is an amino acid selected from the group consisting of proline, alanine, hydroxyproline, dihydroxyproline, thiazolidinecarboxylic acid (thioproline), dehydroproline, pipecolic acid (L-homoproline), azetidinecarboxylic acid, aziridinecarboxylic acid, glycine, serine, valine, leucine, isoleucine and threonine, and wherein the binding between the carboxy terminus of H—[X—Y]$_n$ and the amino group of D occurs via an amide. According to one embodiment, the oligopeptide [X—Y]$_n$ is a tetrapeptide or hexapeptide wherein at least one X is a hydrophobic or aromatic amino acid, alternatively wherein at least one X is a neutral or acidic amino acid or, alternatively, wherein at least one X is a basic amino acid. In a particular embodiment, the amino acids selected for X are L-amino acids. In another embodiment the amino acids selected for Y are L-amino acids or for X and Y are L-amino acids. Another embodiment specifically excludes the use of D-amino acids for X and Y.

In another aspect, the present invention relates to the use of a prodrug of a therapeutic compound D for the manufacture of a medicament for the treatment or prevention of a disease. In a particular embodiment, the present invention relates to the use of a prodrug of a therapeutic compound D for the manufacture of a medicament for the treatment or prevention of a disorder other than cancer or other than a non-infectious disorder associated with elevated levels of DPPIV or other than a disorder which is the consequence of prolonged elevated glucose concentrations in the blood. The therapeutic compound D is not a peptide or a protein, and the therapeutic compound D includes a terminal primary or secondary amino group capable of binding with the carboxylgroup of an amino acid or the therapeutic compound D is bound to a linker comprising a primary or secondary amino group capable of binding with the carboxylgroup of an amino acid, and characterised in that said prodrug comprises said therapeutic compound D linked to an oligopeptide, said oligopeptide consisting of a general structure H—[X—Y]$_n$, wherein X is an amino acid, wherein n is between 1 and 5, wherein Y is an amino acid selected from the group consisting of proline, alanine, hydroxyproline, dihydroxyproline, thiazolidinecarboxylic acid (thioproline), dehydroproline, pipecolic acid (L-homoproline), azetidinecarboxylic acid, aziridinecarboxylic acid, glycine, serine, valine, leucine, isoleucine and threonine, and wherein the binding between the carboxy terminus of H—[X—Y]$_n$ and the amino group of D occurs via an amide. According to one embodiment the disorder other than cancer, other than a disorder associated with elevated levels of DPPIV and other than a disorder which is the consequence of prolonged elevated glucose concentrations in the blood, is selected from the group of bacterial, protozoan, fungal, yeast and viral infections, inflammation, allergy, depression, reduction of pain, neurological disorders, metabolic disorders, respiratory disorders, urologic disorders, cardiovascular disorders, a disorder of the CNS, immunologic disorders and metabolic diseases other than obesity and diabetes. The use of a CD26 cleavable prodrug for the manufacture of a medicament disclaims those disorders which are due to elevated or undesirable levels of DPPIV which can be treated by prodrugs of CD26 inhibitors. It equally disclaims the use for those disorders, such as some type of tumors which have elevated levels of CD26 and which can be treated by CD26 cleavable cytotoxic cancer prodrugs or neoplastic prodrugs. According to another embodiment n ranges from 2 to 5 and more particular n is 2 or 3. According to another embodiment the oligopeptide is a tetrapeptide or hexapeptide, wherein at least one X is an hydrophobic or aromatic amino acid. According to another embodiment the oligopeptide is a tetrapeptide or hexapeptide, wherein at least one X is an neutral or acidic amino acid. According to another embodiment the oligopeptide is a tetrapeptide or hexapeptide, wherein at least one X is a basic amino acid. According to another embodiment the oligopeptide is a tetrapeptide or hexapeptide selected from the group of Val-Pro-[X—Y]$_{1-2}$, more in particular Val-Pro-[X—Y]$_{1-2}$, in order to have a good intestinal absorption, followed by a slow or fast release of the therapeutic compound, depending on the choice of X. According to another embodiment the Y is proline or hydroxyproline, dihydroxyproline or alanine, in a more particular embodiment Y is proline. According to another embodiment, the oligopeptide is coupled via an amide binding to an amino group residing on a aromatic group of a therapeutic compound, residing on a carbohydrate or residing on a nucleoside or on a heterocyclic group or residing on an alkyl, alkenyl or alkynyl or residing on an anorganic molecule. According to another embodiment, the oligopeptide is indirectly coupled to the therapeutic compound D via a linker, said linker comprising an NH$_2$ or substituted NH amino group. According to another embodiment, the therapeutic compound D is a drug for the prevention or treatment of a disorder selected from the group a bacterial, protozoan, fungal, yeast and viral infections, inflammation, allergy, depression, pain, neurological disorders, metabolic disorders, respiratory disorders, urologic disorders, cardiovascular disorders, a disorder of the CNS, immunologic disorders and metabolic diseases other than disorders due to elevated levels of glucose such as obesity and diabetes. In a particular embodiment the therapeutic compound is the antiviral drug TSAO or a derivative thereof such as NAP-TSAO. In another embodiment the antiviral drug is an inhibitor of HIV protease. In a particular embodiment, the amino acids selected for X are L-amino acids. In another embodiment the amino acids selected for Y are L-amino acids or for X and Y are L-amino acids. Another embodiment specifically excludes the use of D-amino acids for X and Y.

Yet another aspect of the invention relates to a manufacturing process for the production of prodrugs using a peptide with general structure H—[X—Y]$_n$ for the preparation of a CD26 cleavable prodrug of a therapeutic compound D. The therapeutic compound D is not a peptide or a protein, and the therapeutic compound D includes a terminal primary or secondary amino group capable of binding with the carboxylgroup of an amino acid or alternatively the therapeutic compound D is bound to a linker comprising a primary or secondary amino group capable of binding with the carboxylgroup of an amino acid The prodrug is characterised in that said prodrug comprises said therapeutic compound D linked to an oligopeptide, said oligopeptide consisting of a general structure H-[X—Y]$_n$, wherein X is an amino acid, wherein n is between 1 and 5, wherein Y is an amino acid selected from the group consisting of proline, alanine, hydroxyproline, dihydroxyproline, thiazolidinecarboxylic acid (thioproline), dehydroproline, pipecolic acid (L-homoproline), azetidinecarboxylic acid, aziridinecarboxylic acid, glycine, serine, valine, leucine, isoleucine and threonine, and wherein the binding between the carboxy terminus of H—[X—Y]$_n$ and the amino group of D or its linker occur via an amide. In a particular embodiment, the amino acids selected for X are L-amino acids. In another embodiment the amino acids selected for Y are L-amino acids or for X and Y are L-amino acids. Another embodiment specifically excludes the use of D-amino acids for X and Y. In one embodiment the peptide has between two to five CD26 cleavable repeats. In another embodiment, the number m of amino acids in the linker $A_m$ between the CD26 cleavable oligopeptide and the therapeutic compound is 1 and A is valine. In another embodiment to CD26 cleavable oligopeptide $[X—Y]_n$ is a tetrapeptide or hexapeptide wherein at least one X is an hydrophobic or aromatic amino acid or alternatively, wherein at least one X is an neutral or acidic amino acid, or alternatively, wherein at least one X is a basic amino acid. In a particular embodiment the oligopeptide $[X—Y]_n$ is a tetrapeptide or hexapeptide selected from the group of Val-Pro-$[X—Y]_{1-2}$ in order to have a good intestinal absorption, followed by a slow or fast release of the therapeutic compound, depending on the choice of X. Within a prodrug construct H—$[X—Y]_n$-D, the therapeutic compound D has a primary ($NH_2$) or secondary (NH) amino group which is bound to the COOH group of the carboxyterminal amino acid of the $[X—Y]_n$ peptide, When the therapeutic compound D has no $NH_2$ or NH group, or the NH or $NH_2$ group can not react (due e.g. steric hindrance), the therapeutic compound D can be reacted with a linker which, after reaction has a $NH_2$ or NH group, which can react with the COON group of the carboxyterminal amino acid of the $[X—Y]_n$ peptide. According to one embodiment Y is proline or hydroxyproline or dihydroxyproline or alanine. In one embodiment the oligopeptide $[X—Y]_n$ is coupled via an amide binding to an amino group residing on a aromatic group of a therapeutic compound, residing on a carbohydrate or residing on a nucleoside or on a heterocyclic group or residing on an alkyl, alkenyl or alkynyl or residing on an anorganic molecule. Alternatively, the oligopeptide $[X—Y]_n$ is indirectly coupled to the therapeutic compound D via a linker comprising an amino group. Such a linker can have any structure, including but not limited to the structure of an oligopeptide $A_m$ wherein m ranges between 1 to 15 and more particularly between 1 to 3, or m=1. A in the structure $A_m$ can be any amino acid. According to one embodiment m=1 and A is valine. A prodrug which such a linker has a general structure H—$[X—Y]_n$-$A_m$-D. The oligopeptide $A_m$ or the amino acid A is linked at its aminoterminus via an amide binding to the oligopeptide H—$[X—Y]_n$. The oligopeptide $A_m$ or the amino acid A is linked at its carboxy terminus via an amide or ester binding to the therapeutic compound D. Pharmaceutical compositions can comprise prodrugs of drugs for the prevention or treatment of a disorder selected from the group a bacterial, protozoan, fungal, yeast and viral infections, inflammation, allergy, depression, pain, neurological disorders, metabolic disorders, respiratory disorders, urologic disorders, cardiovascular disorders, a disorder of the CNS, immunologic disorders and metabolic diseases other than disorders due to elevated levels of glucose such as obesity and diabetes. A particular example of an antiviral drug is TSAO. Another particular example of an antiviral drug is an HIV protease inhibitor, reverse transcriptase inhibitor or integrase inhibitor.

In a particular embodiment, the invention relates to a therapeutic compound D coupled to two or more oligopeptides at different sites of the therapeutic compound.

DETAILED DESCRIPTION OF THE INVENTION

Definitions

Figure 1:
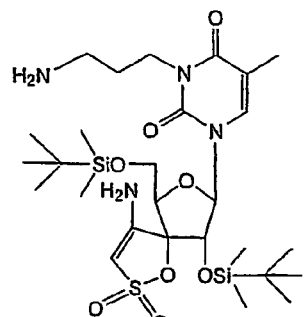
FIG. 1 presents the structural formulae of a number of representative test compounds.
Figure 1:
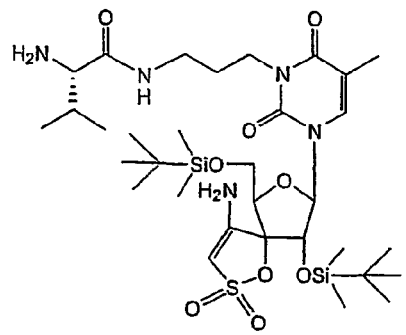
Figure 1:
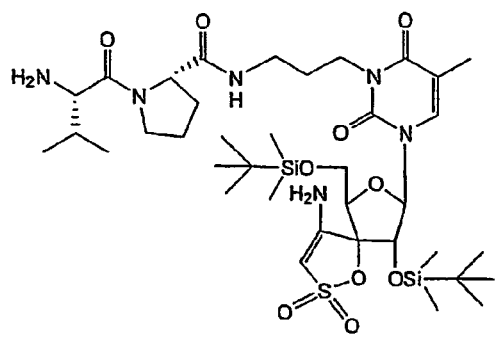
Figure 1:
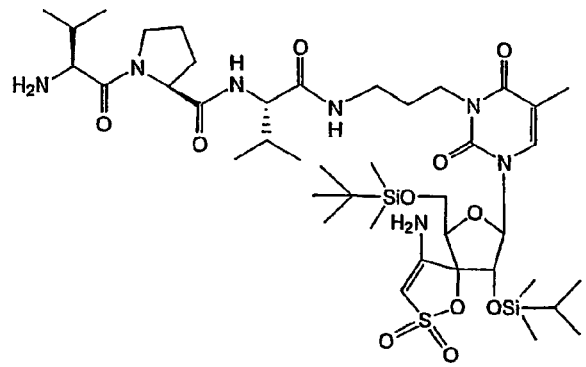
Figure 1:
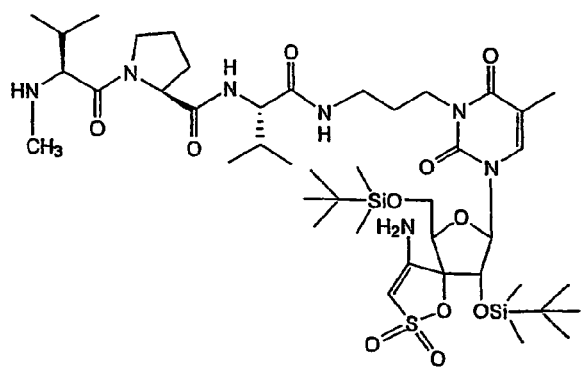

The term "prodrug or prodrugs" as used herein refers to mostly inactive derivatives (or derivatives with strongly reduced activity, i.e. less than 20%, less that 10%, less than 5% or even less than 1% residual activity of the underived drug molecule) of a therapeutic compound that require a chemical or enzymatic transformation in order to release the active parent drug. The prodrug of the present invention has a general structure H—[X—Y]$_n$-D. The chemical nature of this prodrug is explained in detail below. Prodrugs are designed to overcome an undesirable property of a drug. As such this technology can be applied to improve the physicochemical, biopharmaceutical and/or pharmacokinetical properties of various drugs. Usually, the prodrug as such is biologically inactive. Therefore, prodrugs need to be efficiently converted to the parent drugs to reach pronounced efficacy as soon as the drug target has been reached. This activation can be done by enzymes, which are present in the body, alternatively the enzymes are co-administrated with the prod rug.

In general, prodrugs are designed to improve the penetration of a drug across biological membranes in order to obtain improved drug absorption, to prolong duration of action of a drug (slow release of the parent drug from a prodrug, decreased first-pass metabolism of the drug), to target the drug action (e.g. brain or tumor targeting, lymphocyte targeting), to modify, mostly improve aqueous solubility and stability of a drug (i. v. preparations, eyedrops, etc.), to improve topical drug delivery (e.g. dermal and ocular drug delivery), to improve the chemical/enzymatic stability of a drug (e.g. peptides) or to decrease drug side-effects, more in general in order to improve efficacy of a therapeutic compound D.

The term "therapeutic compound D" as used herein refers to any agent having a beneficial effect on a disease, any agent that is or will be used in the future as a therapy for a certain disease or disorder. This refers also to all molecules which are still in the discovery or development phase and which have not proven their efficacy and safety yet. This includes small organic molecules, proteins, peptides, oligonucleotides, carbohydrates, aliphatic carbon chains, aromatic compounds and analogs and derivatives.

The therapeutic compound D with a (terminal) amino group, more in particular a primary or secondary amino group, refers to therapeutic compounds with a free amino group (primary or secondary), namely a NHR group, wherein R can be hydrogen or any other chemical group known in the art. The amino group can be coupled to the therapeutic compound D via a saturated or unsaturated carbon, to carbonyl, or can be part of other broader functionalities (amide, carbamate, etc.) wherein the amino group is comprised, but the amino group in each circumstance has to be able to react with an amino acid in order to form stable amide bonds. In a particular embodiment, the amino group NHR of the therapeutic compound belongs to the functional group of amine functions and does not belong to a broader general functionality such as amides or carbamates.

The therapeutic drug can also be linker to an oligopeptide through a linker. This linker can have any organic structure, thereby including amino acids, and contains a NHR group as described above.

"CD26" as used herein refers to the dipeptidyl-peptidase IV (EC 3.4.14.5) in its membrane bound and free form. Synonyms for CD26 are DPPIV, DPP4, CD26/DPPIV or ADCP2 (adenosine deaminase complexing protein 2) As used herein, "dipeptidyl-peptidase (s)" refers to enzymes with a dipeptidyl aminopeptidase activity, i.e removing a dipeptide from the aminoterminal side of a substrate side by cleavage of the second CO—NH amide bond in the substrate. Other enzymes than CD26 with a comparable activity and proteolytic specificity as CD26 (i.e. prolyloligopeptidases) are referred to by "dipeptidyl-peptidase(s)". "Dipeptidyl-peptidase IV" refers to CD26.

As written herein, amino acid sequences are presented according to the standard convention, namely that the amino terminus of the peptide is on the left and the carboxy terminus is on the right.

As used herein, the term "peptide" or "oligopeptide" relates to two or more amino acids which are connected by amide bindings. When mentioned in conjunction with a therapeutic compound D, the peptide or oligopeptide refers to two or more amino acids which are connected by an amide binding, originating from a COOH group of the peptide and a NH$_2$ or NH group on the therapeutic compound D or a linker connected to the therapeutic drug. The length of a peptide is indicated by greek numbers preceding the word-peptide (dipeptide, tripeptide, tetrapeptide, pentapeptide, hexapeptide, heptapeptide, octapeptide, nonapeptide, decapeptide, etc.). When referred to as [X—Y]$_n$, each X and Y in each repeat unit [X—Y] are chosen independently from one another and independently for each repeat unit.

In the present invention, a new prodrug technology is provided based on the coupling of a peptide to a therapeutic agent, whereby the amide bond of the conjugates is cleavable by a dipeptidyl-peptidase, such as CD26. As such, the solubility, bioavailability and the efficacy of the therapeutic compound D in general can be modulated more extensively. The lymphocyte surface glycoprotein CD26 belongs to a unique class of membrane-associated peptidases. It is characterized by an array of diverse functional properties and it is identical to dipeptidyl-peptidase IV (DPP IV, EC 3.4.14.5). DPP IV is a member of the prolyl oligopeptidase (POP; EC3.4.21.26) family, a group of atypical serine proteinases able to hydrolyze the prolyl bond. The 766-amino acid long CD26 is anchored to the cellular lipid bilayer membrane by a single hydrophobic segment, and has a short cytoplasmic tail of six amino acids [Abbott et al. *Immunogenetics* (1994) 40: 331-338]. The membrane anchor is linked to a large extracellular glycosylated region, a cysteine-rich region and a C-terminal catalytic domain (Abott et al. cited supra). CD26 is strongly expressed on epithelial cells (i.e. kidney proximal tubules, intestine) and on several types of endothelial cells and fibroblasts, as well as leukocyte subsets [Hegen, M. In: Leukocyte Typing VI. Kishimoto, T., ed. Garland Publishing, (1997), pp. 478-481]. CD26 also occurs as a soluble form present in seminal fluids, plasma and cerebrospinal fluid. It lacks the intracellular tail and the transmembrane region [De Meester et al. *Rev. Immunol. Today* (1999) 20: 367-375]. In addition to its exopeptidase activity, CD26 specifically binds to several proteins outside its substrate-binding site [i.e. adenosine deaminase [Trugnan et al. In: Cell-Surface Peptidases in Health and Disease. Kenny, & Boustead" eds. BIOS, (1997), pp. 203-217], fibronectin [Gonzalez-Gronow, et al. *Fibrinolysis* (1996), 10 (Suppl. 3): 32], collagen [Loster et al. *Biochem. Biophys Res. Commun.* (1995), 217: 341-348]. CD26 is endowed with an interesting (dipeptidyl) peptidase catalytic activity and it has a high selectivity for peptides with a proline or alanine at the penultimate position of the N-terminus of a variety of natural peptides.

Several cytokines, hematopoietic growth factors, neuropeptides and hormones share the X-Pro or X-Ala motif at their N-terminus and have been shown to act as efficient substrates for the enzyme [reviewed in De Meester et al. *Rev. Immunol. Today* (1999) 20: 367-375 and Mentlein *Regul. Pept.* (1999) 85: 9-24]. Substance P is even an example of a natural peptide of 11 amino acids containing an Arg-Pro-Lys-Pro [SEQ ID NO:1] sequence at its H-terminus, and which is cleaved by CD26 to an active heptapeptide by stepwise release of Arg-Pro and Lys-Pro [Ahmad et al. *Pharmacol. Exp. Ther.* (1992), 260: 1257-1261]. CD26 can cut dipeptides from very small natural peptides [i.e. the pentapeptide enterostatin (Val-Pro-Asp-Pro-Arg) [SEQ ID NO:2] [Bouras et al. *Peptides* (1995), 16: 399-405] to larger peptides [including the chemokines RANTES and SDF-1α and IP-10 (68 to 77 amino acids)] containing respectively the Ser-Pro, Lys-Pro and Val-Pro sequences at their amino terminus [Oravecz et al. *J. Exp. Med.* (1997), 186: 1865-1872; Proost et al. *J. Biol. Chem.* (1998), 273: 7222-7227; Ohtsuki et al. *FEBS Lett.* (1998), 431: 236-240; Proost et al. *FEBS Lett.* (1998), 432: 73-76].

Although a relatively restricted substrate specificity (penultimate Pro or Ala) has been observed for CD26, lower cleavage rates have also sometimes been observed when the penultimate amino acids were Gly, Ser, Val or Leu instead of Pro or Ala (De Meester et al. cited supra). Also, the nature of the terminal amino acid plays a role in the eventual catalytic efficiency of CD26.

There is a decreasing preference from hydrophobic (i.e. aliphatic: Val, Ile, Leu, Met and aromatic Phe, Tyr, Trp) to basic (i.e. Lys, Arg, His) to neutral (i.e. Gly, Ala, Thr, Cys Pro, Ser, Gln, Asn) to acidic (i.e. Asp, Glu) amino acids as the preferred first amino acid at the amino terminus for efficient cutting of the peptide by CD26 (De Meester et al. cited supra). Also unnatural amino acids are recognised. The observation that a double truncation of macrophage-derived chemokine (MDC) by CD26 can occur thereby sequentially loosing Gly$^1$-Pro$^2$ followed by Tyr$^3$-Gly$^4$, suggests that the substrate activity of CD26 may be less restricted to the penultimate Pro or Ala than generally accepted [Proost, P. et al. *J. Biol. Chem.* (1999), 274: 3988-3993].

Many other hydrolases (EC 3), more specifically peptidases (EC 3.4) and yet more specifically aminopeptidases (EC 3.4.11) such as prolyl aminopeptidase (EC 3.4.11.5) and X-Pro aminopeptidase (EC 3.4.11.9) have already been identified. Also other dipeptidases (EC 3.4.13), peptidyl-dipeptidases (EC 3.4.15) and dipeptidyl-peptidases (EC 3.4. 14, this EC-group also includes tripeptidyl-peptidases) exist next to CD26. Dipeptidyl-peptidase I (EC 3.4.14.1) occurs in the lysosome and cleaves a dipeptide from a peptide with consensus sequence $X_1$—$X_2$—$X_3$ except when $X_1$ is Arg or Lys or $X_2$ or $X_3$ is Pro. Dipeptidyl-peptidase II (EC 3.4.14.2) is a lysosomal peptidase that is maximally active at acidic pH and releases dipeptides from oligopeptides (preferentially tripeptides) with a sequence $X_1$—$X_2$—$X_3$ wherein $X_2$ preferably is Ala or Pro. DPP III (EC 3.4.14.4) is a cytosolic peptidase and cleaves dipeptides from a peptide comprising four or more residues dipeptidyl-dipeptidase (EC 3.4.14.6). X-Pro dipeptidyl-peptidase (EC 3.4.14.11) is a microbial peptidase with similar activity to CD26. Some of them are found in humans and other mammals, while others are produced by microorganisms such as yeast and fungi. They differ in first instance in amino acid sequence, but also in their specificity for recognizing amino acid sequences. In addition, database screening with DPPIV revealed novel proline specific dipeptideases (DPP8, DPP9, DPP10) [Qi et al. *Biochem J.* (2003) 373, 179-189]. Most of these proline specific dipeptidases occur intracellularly in the lysosome and act at acidic pH. Only DPPIV occurs as a membrane bound protein at the outside of a cell or as a secreted protein. Thus according to one embodiment, the compounds of the present invention are cleavable by an extracellular or membrane bound dipeptidyl peptidase at neutral pH.

The present invention demonstrates that peptidyl prodrug derivatives are efficiently converted to the parent compound by the exodipeptidyl-peptidase activity of CD26. The present invention further demonstrates that the peptidyl prodrug derivatives are extracellularly processed to the parent therapeutic compound.

Since an L-valine moiety can be involved in the dipeptidyl prodrug approach, this technology may represent a powerful tool to make lipophilic compounds not only markedly more water-soluble and less protein binding, but also to enhance oral bioavailability and plasma delivery of the parent molecule. The technology may also represent a powerful tool to ensure a more selective delivery of the parent drug to CD26-expressing cells.

The present invention is derived from the knowledge that dipeptidyl-peptidase IV (CD26) has a postproline or postalanine dipeptidyl aminopeptidase activity, preferentially cleaving X-proline or X-alanine dipeptides from the N-terminus of polypeptides or proteins.

In view of this observation, the present invention provides a new prodrug technology in order to modulate the solubility, plasma protein binding and/or to enhance the bioavailability of a drug. In other embodiments of the invention, prodrugs are delivered in order to more selectively target drugs, to enhance brain and lymphatic delivery of drugs and/or to extend drug half-lives in plasma. The present invention provides new prodrugs, characterized in that the prodrugs are cleavable by the dipeptidyl-peptidase CD26 or other enzymes with the same activity and proteolytic specificity as CD26. In a preferred embodiment, the prodrugs of the present invention are peptide-therapeutic compound conjugates and derivatives thereof, that include amino acid sequences containing cleavage sites for dipeptidyl-peptidases, such as CD26. As such, the invention also provides a therapeutic prodrug composition comprising a therapeutic compound D linked to a peptide via an amide bond, which is specifically cleaved by dipeptidyl-peptidases, such as CD26.

The therapeutic compound D can be linked to the carboxy group of an amino acid either directly or through a linker group. In a preferred embodiment, the therapeutic compound D and the peptide are directly coupled via an amide bond. The therapeutic compound D can have a free amino group (primary or secondary that can be coupled with the carboxyl group of amino acids, more preferably with the α-carboxyl group. In another preferred embodiment, the therapeutic compound D and the peptide are coupled via a linker, wherein the linker can be of non-peptidic or peptidic nature. If the connection between the therapeutic compound D and the peptide is made through a linker, the connection between the linker and the first amino acid is preferably an amide bond. The linker may be connected to the therapeutic compound D through any bond types and chemical groups known to those skilled in the art, more preferably by covalent bonding. The linker may remain on the therapeutic compound D indefinitely after cleavage, or may be removed thereafter, either by further reactions with agents present in the mammal or in a self-cleaving step. External agents which may affect cleavage of the linker include enzymes, proteins, organic or inorganic reagents, protons and other agents. In embodiments in which the linker remains attached to the drug, the linker can be any group which does not substantially inhibit the activity of the drug after cleavage of the peptide. In other embodiments, the linker is self-cleaving. Self-cleaving linkers are those which are disposed to cleave from the drug after the cleavage of the peptide by dipeptidyl-peptidases, such as CD26. Mechanisms involved in the self-cleavage of the linkers are for example intra molecular cyclisation or spontaneous $S_N1$ solvolysis and release the drug upon peptide cleavage. Some examples of linkers are provided in Atwell et al. (Atwell et al. *J. Med. Chem.* 1994, 37: 371-380). The linkers generally contain primary amines which form amide bonds to the carboxy terminus of the peptide. The linkers can also contain a carboxylic acid which forms an amide bond to a primary amine found on the drug. The linker can be coupled to the drug by one or more reactions chosen from the reactions available to the person skilled in the art.

In an embodiment the linker between the CD26 cleavable peptides (consisting of one or more repetitive X—Y dipeptides with structure $[X—Y]_n$ which is cleavable by CD26) and the therapeutic compound of the present invention comprise one or more aminoacids and have in a more particular embodiment a general structure $[X—Y]_n$-$A_m$. Herein A is any amino acid. The binding between the $[X—Y]_n$ oligopeptide and the consecutive A amino acid is an amide binding to allow CD26 proteolysis. The binding between two A amino acids can be either an amide binding or an ester binding and between an A amino acid and the prodrug can be either an amide binding or an ester binding or any other binding known in the art. m can vary in length between 1 to 15. In one embodiment m is 1 and A can be hydrolyse from the prodrug by an esterase or an aminopeptidase.

In one embodiment the protease which can be used for proteolysis of the prodrug is CD26. The obtained experimental data reveal that CD26 relies for its cleavage only on the dipeptide structure. Its activity is not hampered by the presence of the therapeutic compound D immediately after the amide bond between proline and the drug moiety. In the same context, there is thus no need to have additional peptide or other linker molecules between the dipeptide or polypeptide and the drug. Furthermore, due to its tissue expression (on both cancer and normal tissue) on different organs (from high level to lower levels: kidney, lung, adrenal gland, jejunum, liver, glandula parotis, spleen, testis and also on skin, heart, pancreas, brain, spinal cord, serum), and different cell types (such as thymocytes, endothelial cells, lympfocytes, microglial cells), several applications and several therapeutic applications can be envisaged. The rate of proteolysis of a peptide can be modulated by modifying the aminoterminal aminoacid and/or the second aminoacid. Together or independently of the modulation of hydrolysis, the physicochemical character of the peptide prodrug can be modified.

Particularly, the aminoterminal end of the peptide in the prodrug comprises X-Pro, X-Ala, X-Gly, X-Ser, X-Val, or X-Leu, wherein X represents any amino acid or isomers (i.e. L- or D-configuration) thereof. Other dipeptides, with on the second position hydroxyproline, dihydroxyproline, thiazolidinecarboxylic acid (thioproline), dehydroproline, pipecolic acid (L-Homoproline), azetidinecarboxylic acid, and aziridinecarboxylic acid are also cleavable by CD26. In a preferred embodiment, the peptide comprises aminoterminally X-proline or X-alanine. As such the amino acids can be selected from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine and derivatives thereof. Also modified (i.e. hydroxylproline) or unnatural amino acids can be included. In another preferred embodiment, the length of the peptide is between 2 and 10 amino acids and can therefore have a length of 2, 3, 4, 5, 6, 7, 8, 9 or 10 amino acids. In another preferred embodiment, the peptide comprises $[X—Y]_n$ repeated units wherein X represents any amino acid, Y is selected from Pro, Ala, Gly, Ser, Val or Leu and n is selected from 1, 2, 3, 4 or 5. In another more preferred embodiment, said peptide is a dipeptide. In still a more preferred embodiment, the dipeptide is Lys-Pro. In another still more preferred embodiment, the amino acids have the L-configuration. The present experiments seem to show that the aminoterminus of the peptide of the prodrug containing conventional capping groups or protection groups is not or very weakly cleaved and thereby does not seem to be a substrate for CD26. Such capping groups include acetyl, succinyl, benzyloxycarbonyl, glutaryl, fluorenylmethyloxycarbonyl (Fmoc), tert-Butyloxycarbonyl (Boc), morpholinocarbonyl, methyl and many others known in the art. In one embodiment, the terminal amino group of the terminal amino acid of the peptide of the prodrugs, contains no capping or protection groups. A particular embodiment of the present invention excludes the use of prodrugs without a free terminal amino group. Those skilled in the art can make substitutions to achieve peptides with better profile related to solubility, bioavailability and targeting of the conjugate. Therefore, the invention includes the peptide sequences as described above, as well as analogs or derivatives thereof, as long as the conjugates remain cleavable by dipeptidyl-peptidase, such as CD26.

In another embodiment the CD26 cleavable oligopeptide $[X—Y]_n$ is a peptide wherein at least one X is a hydrophobic or aromatic amino acid or alternatively, wherein at least one X is an neutral or acidic amino acid, or alternatively, wherein at least one X is a basic amino acid. To modulate hydrophobicity and/or proteolysis rate of longer peptides (n is 3, 4, 5) more than one X will have the specific type of side chains to achieve the desired effect. Also the choice of Y will influence the proteolysis rate, the hydrophobicity, solubility, bioavailability and the efficacy of the prodrug.

In yet another embodiment, the peptides with a general structure $[X—Y]_n$ are tetrapeptides or hexapeptides with a structure selected from the group of XF—Y—XF—Y, XF—Y—XS—Y, XS—Y—XF—Y, XS—Y—XS—Y XB—Y—X—Y, X—Y—XB—Y and XB—Y—XB—Y or a hexapeptide with a structure selected from the group of XF—Y—XF—Y—XF—Y, XS—Y—XF—Y—XF—Y, XF—Y—XS—Y—XF—Y, XF—Y—XF—Y—XS—Y, XF—Y—XS—Y—XS—Y, XS—Y—XF—Y—XS—Y, XS—Y—XS—Y—XF—Y and XS—Y—XS—Y—XS—Y, XB—Y—X—Y—X—Y, XB—Y—XB—Y—X—Y, X—Y—XB—Y—XB—Y, XB—Y—X—Y—XB—Y and XB—Y—XB—Y—XB. Herein F stands for fast and XF is an amino acid that results in a rapid release of a dipeptide by CD26 (for example aromatic and hydrophobic amino acids). Herein S stands for slow and XS is an amino acid that causes a slow release of a dipeptide by CD26 (for example acidic and neutral amino acids such as Aspartic acid and Glutamic acid). Herein B stands for basic and XB is a basic amino acid (Lys, Arg and His) leading to a moderate release of a charged and hydrophilic dipeptide. Such combinations allow tailor-made combinations of peptides that give a prodrug a well defined rate of degradation together with a defined hydrophobicity. For example the degradation of a hydrophobic prodrug with Tyr/Phe-Pro dipeptide can be delayed by the presence of an additional aminoterminal Gly-Pro dipeptide, resulting in a Gly-Pro-Tyr-Pro [SEQ ID:NO:3] Gly-Pro-Phe-Pro [SEQ ID NO:12] tetrapetide prodrug. Hydrophobicity can even be increased by adding an additional Tyr/Phe-Pro dipeptide leading to the exapeptides such as e.g. Gly-Pro-Tyr-Pro-Tyr-Pro [SEQ ID NO:4]. If a charged peptide prodrug with slow release is desired, Asp-Pro-Lys-Pro [SEQ ID NO:5] might be preferred over Gly-Pro. Other combinations can be developed by the skilled person wherein a tetrapeptide or hexapeptide allows the modulation of solubility and degradation rate of a peptide prodrug by CD26. For other purposes, proline can be replaced by alanine. The physicochemical properties and degradation rate of an undigested, partially digested and completely digested prodrug can be evaluated by determination of its retention time on reversed phase chromatography.

The therapeutic compounds that may be used in the prodrugs of the invention include any drugs (except from protein or peptide drugs such as peptide hormones) that can be directly or indirectly linked to a peptide and whereby the conjugate is cleavable by a dipeptidyl-peptidase, such as CD26. In addition to known therapeutic compounds, this invention can also be applied to the novel drug molecules that are currently under drug development or to drug molecules which are already in clinical use. In another preferred embodiment, the therapeutic compound D is a small organic molecule and not a peptide, protein, an intercalator or an oligonucleotide or analogs thereof (such as HNA, PNA, etc.). The therapeutic molecule can have an activity in the cardiovascular, neurological, respiratory, oncology, metabolic diseases, immunology, urology, anti-infectives, inflammation and all other therapeutic fields. In yet another more preferred embodiment, the therapeutic compound D has an antiviral activity. In still a more preferred embodiment, the therapeutic compound D has an anti-HIV activity.

Preferred drugs/therapeutic compounds are those containing primary amines, more in particular belonging to an amine function. The presence of a primary amine allows the formation of an amide bond between the drug and the peptide. The primary amines may be found in the drugs as commonly provided, or they may be added to the drugs by chemical synthesis. Certain therapeutic compounds contain primary amines, for example, anthracycline antibiotics containing an amino sugar such as doxorubicin, daunorubicin, epirubicin, idarubicin and the like. Antiviral drugs that contain an amine or amide are for example the guanine derivatives with antiherpes activity like acyclovir, gancyclovir, penciclovir and lobucavir, the cytosine derivatives gemcitabine, ddC, araC, HPMPC (Cidofovir) and lamivudine (3TC), the protease inhibitors amprenavir and DMP850 and 851. Others are ribavirin, the NNRTIs TMC 125 (from Tibotec-Virco) and AG 1549 (from Agouron), PMPA (tenofovir), PMEA (adefovir) and oseltamivir. Other therapeutic compounds that can be transformed to prodrugs of the invention are for example: DNA intercalators such as actinomycin D, adriamycin, amino acridines (proflavine); DNA binders such as cisplatin (cis-diamino platinum dichloride); DNA chain cutting agents such as bleomycin; Hormones such as noradrenaline; Alkaloids such as procaine (novocaine); Antidepressants such as phenylzine; Neurotransmitters such as dopamine and GABA (y-aminobutanoic acid); Anticancer agents such as phosphoramide mustard and methotrexate; Antibiotics such as sulfonamides (benzenesulfonamides, prontosil, sulfonilamide, sulfadiazine, sulfamethoxine, etc.) and aminoglycosides such as streptomycin; Vitamins such as folic acid, tetrahydrofolic acid, etc; Antimalarial agents such as trimethoprim; Anti-lepra agents such as sulfones.

According to the FDA's Biopharmaceutics Classification System (BCS), drug substances are classified as follows: Class I—High Permeability, High Solubility; Class II—High Permeability, Low Solubility; Class III—Low Permeability, High Solubility and Class IV—Low Permeability, Low Solubility. How drugs are classified in this classification system is described in the guidelines of the BCS. In a preferred embodiment, the therapeutic compounds D that can be used in the invention are selected from class 11, 111 and IV.

The invention provides for prodrugs that are cleavable by dipeptidyl-peptidases. The dipeptidyf-peptidases can be selected from the group of peptidases (EC 3.4) and yet more specifically aminopeptidases (EC 3.4.11) such as prolyl aminopeptidase (EC 3.4.11.5) and X-Pro aminopeptidase (EC 3.4.11.9), from the group of dipeptidases (EC 3.4.13), peptidyl-dipeptidases (EC 3.4.15) and dipeptidyl-peptidases (EC 3.4.14, this EC-group also includes tripeptidyl-peptidases) such as dipeptidyl-peptidase I (EC 3.4.14.1), II (EC 3.4.14.2), III (EC 3.4.14.4), IV (EC 3.4.14.5), dipeptidyl-dipeptidase (EC 3.4.14.6) and X-Pro dipeptidyl-peptidase (EC 3.4.14.11). In a preferred embodiment, the prodrug is cleavable by dipeptidyl-peptidases present in mammals or more preferably in humans. In a more preferred embodiment, the prodrug is cleavable by dipeptidyl-peptidase IV (CD26), as well by the cell-surface bound as by the soluble form present in seminal fluids, plasma and cerebrospinal fluid. The occurrence of two different types of CD26 allows the application of prodrugs for activation at the cell membrane and for activation in body fluids.

The invention also provides a method for modulating (i.e. increasing, decreasing) the (water) solubility, the protein binding and/or the bioavailability of a therapeutic compound D by coupling a peptide to said therapeutic compound D whereby the resulting conjugate is cleavable by a dipeptidyl-peptidase, such as CD26. Any change of the therapeutic compound D, also including conjugation of amino acids, has a proven influence on the solubility and bioavailability profile of said drug. The present invention provides however a method of ameliorating the solubility and/or bioavailability of the drug without changing the activity profile of the therapeutic compound D. Other chemical groups may be coupled to the prodrugs of the invention, including those which render the prodrug more soluble in water. These groups include polysaccharides or other polyhydroxylated moieties. For example, dextran, cyclodextrin and starch may be included in the prodrug of the invention.

The present invention also provides a method for targeting molecules to dipeptidyl-peptidase expressing cells, tissues or organs, provided that the dipeptidyl-peptidases are expressed on the cell surface or secreted in the extracellular medium. CD26 is expressed in a variety of organs, primarily on apical surfaces of epithelial and acinar cells and at lower levels on lymphocytes and capillary endothelial cells. CD26 has been demonstrated in the gastrointestinal tract, biliary tract, exocrine pancreas, kidney, uterus, placenta, prostate epidermis, muscle, adrenal gland, parotid gland, sweat gland, salivary gland, mammary gland, and on epithelia of all organs examined including liver, spleen, lungs and brain. In one embodiment, CD26 cleavable prodrugs can be used for the treatment of non-cancer disorders or dysfunctions, wherein DPPIV levels are increased, such as liver regeneration, hepatic dysfunction, kidney transplant rejections, encephalitis or osteoporosis.

In another embodiment, CD26 cleavable prodrugs can be used for the treatment or prevention of metabolic anomalies such as excess weight, glucosuria, hyperlipidaemia and also possible serious metabolic acidoses and diabetes mellitus, which are a consequence of prolonged elevated glucose concentrations in the blood.

In another embodiment, CD26 cleavable prodrugs can be used for the treatment or prevention of any disorder of dysfunction of one of the above mentioned tissues wherein CD26 occurs at normal levels.

In another embodiment, CD26 cleavable prodrugs can be used for the treatment or prevention of any disorder of dysfunction in one of the above mentioned organs or tissues, even under conditions wherein CD26 levels are lowered but still present such as major depression, norexai and buimia nervosa, diabetes mellitus, hypertension, rheumatoid arthritis, Systemic lupus erythematosus, pregnancy, immunosuppression, viral infections such as HIV, or certain cancers such as nonhepatic gastrointestinal cancer and oral squamous cell carcinoma.

The present invention furthermore provides a method of producing a prodrug, wherein the prodrug is cleavable by a dipeptidyl-peptidase, such as CD26. This method of producing a prodrug comprises the step of linking a therapeutical active drug and a peptide. In a more preferred embodiment, the therapeutical active drug or the peptide are in a first step derivatised in order to be able to link the therapeutic compound D and the peptide in a later step via an amide binding. In certain embodiments, the peptide is linked directly to the drug. In other embodiments, the peptide is indirectly linked to the drug, the linkage occurring through a linker. In each case the carboxy terminus of the peptide is used for linking. Many acceptable methods of coupling carboxyl and amino groups to form amide bindings are known to those skilled in the art.

The present invention furthermore provides for prodrugs of TSAO. Peptide prodrugs of [1-[2',5'-Bis-O-(tert-butyldimethylsilyl)-beta-D-ribofuranosyl]-3-(3-amino-propyl)-thymine]-(R)(ribo)-3'-spiro-5-(4-amino-1,2-oxathiole-2,2-dioxide) (=NAP-TSAO) are provided by this invention. The valine-, valine-proline- and valine-proline-valine-NAP-TSAO derivatives are provided by this invention.

The present invention furthermore provides for prodrugs of AraC, doxorubicin and acyclovir.

In one particular embodiment, the present invention relates to prodrug compounds of formula (I)

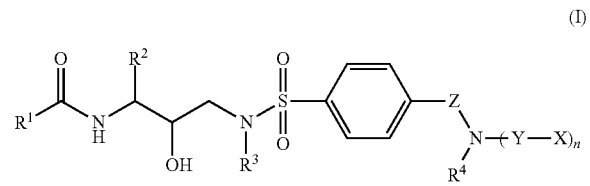

(I)

the stereoisomeric forms and salts thereof,
wherein n is 1, 2, 3, 4 or 5;
Y is proline, alanine, hydroxyproline, dihydroxyproline, thiazolidinecarboxylic acid (thioproline), dehydroproline, pipecolic acid (L-homoproline), azetidinecarboxylic acid, aziridinecarboxylic acid, glycine, serine, valine, leucine, isoleucine and threonine;
X is selected from any amino acid in the D- or L-configuration;
X and Y in each repeat of [Y—X] are chosen independently from one another and independently from other repeats;
Z is a direct bond or a bivalent straight or branched saturated hydrocarbon group having from 1 to 4 carbon atoms;
$R^1$ is an aryl, heteroaryl, aryloxy, heteroaryloxy, aryloxy$C_{1-4}$alkyl, heterocycloalkyloxy, heterocycloalkyl$C_{1-4}$alkyloxy, heteroaryloxy$C_{1-4}$ alkyl, heteroaryl$C_{1-4}$alkyloxy;
$R^2$ is aryl$C_{1-4}$alkyl;
$R^3$ is $C_{1-10}$alkyl, $C_{2-6}$alkenyl or $C_{3-7}$cycloalkyl $C_{1-4}$alkyl;
$R^4$ is hydrogen or $C_{1-4}$alkyl;
aryl, when used alone or in combination with another group, means phenyl optionally substituted with one or more substituents each individually selected from the group consisting of $C_{1-4}$alkyl, hydroxy, $C_{1-4}$alkyloxy, nitro, cyano, halo, amino, mono- or di($C_{1-4}$alkyl)amino and amido;
heteroaryl, when used alone or in combination with another group, means a monocyclic or bicyclic aromatic heterocycle having one or more oxygen, sulphur or nitrogen heteroatoms, which aromatic heterocycle may optionally be substituted on one or more carbon atoms with a substituent selected from the group consisting of $C_{1-4}$alkyl, $C_{1-4}$alkyloxy, amino, hydroxy, aryl, amido, mono- or di($C_{1-4}$alkyl)amino, halo, nitro, heterocycloalkyl and $C_{1-4}$alkyloxycarbonyl, and which aromatic heterocycle may also be optionally substituted on a secondary nitrogen atom by $C_{1-4}$alkyl or aryl$C_{1-4}$alkyl,
heterocycloalkyl, when used alone or in combination with another group, means a saturated or partially unsaturated monocyclic or bicyclic heterocycle having one or more oxygen, sulphur or nitrogen heteroatoms, which heterocycle may optionally be substituted on one or more carbon atoms with a substituent selected from the group consisting of $C_{1-4}$alkyl, $C_{1-4}$alkyloxy, hydroxy, halo and oxo, and which heterocycle may also be optionally substituted on a secondary nitrogen atom by $C_{1-4}$alkyl or aryl$C_{1-4}$alkyl.

The term $C_{1-4}$alkyl as a group or part of a group means straight and branched chained saturated monovalent hydrocarbon radicals containing from 1 to 4 carbon atoms. Examples of such $C_{1-4}$alkyl radicals include methyl, ethyl, n-propyl, isopropyl, n-butyl, isobutyl, sec-butyl, tert-butyl, 2-methylbutyl, pentyl, iso-amyl, hexyl, 3-methylpentyl and the like.

The term $C_{1-6}$alkyl as a group or part of a group means straight and branched chained saturated monovalent hydrocarbon radicals containing from 1 to 6 carbon atoms. Examples of such $C_{1-6}$alkyl radicals include methyl, ethyl, n-propyl, isopropyl, n-butyl, isobutyl, sec-butyl, tert-butyl, 2-methylbutyl, pentyl, iso-amyl, hexyl, 3-methylpentyl and the like.

The term $C_{1-10}$alkyl as a group or part of a group means straight and branched chained saturated monovalent hydrocarbon radicals containing from 1 to 10 carbon atoms. Examples of such $C_{1-10}$alkyl radicals include the examples of C 6alkyl radicals and heptyl, octyl, nonyl, decyl, 3-ethylheptyl and the like.

$C_{2-6}$alkenyl as a group or part of a group means straight and branched chained monovalent hydrocarbon radicals having at least one double bond and containing from 2 to 6 carbon atoms. Examples of such $C_{2-6}$alkenyl radicals include ethenyl, propenyl, 1-butenyl, 2-butenyl, isobutenyl, 2-methyl-1-butenyl, 1-pentenyl, 2-pentenyl, 1-hexenyl, 2-hexenyl, 3-hexenyl, 3-methyl-2-pentenyl and the like.

The term "halo" or "halogen", when used alone or in combination with another group, is generic to fluoro, chloro, bromo or iodo.

The term $C_{3-7}$cycloalkyl, when used alone or in combination with another group, is generic to cyclopropyl, cyclobutyl, cyclopentyl, cyclohexyl and cycloheptyl.

For therapeutic use, the salts of the prodrug compounds of the present invention are those wherein the counter-ion is pharmaceutically or physiologically acceptable. However, salts having a pharmaceutically unacceptable counter-ion may also find use, for example, in the preparation or purification of a pharmaceutical acceptable compound of the present invention. All salts, whether pharmaceutical acceptable or not are included within the ambit of the present invention.

The pharmaceutically acceptable or physiologically tolerable acid addition salt forms which the prodrug compounds of the present invention are able to form can conveniently be prepared using the appropriate acids, such as, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-amino-salicylic, pamoic and the like acids.

Conversely said acid addition salt forms can be converted by treatment with an appropriate base into the free base form.

The prodrug compounds of the present invention containing an acidic proton may also be converted into their non-toxic metal or amine addition salt form by treatment with appropriate organic and inorganic bases. Appropriate base salt forms comprise, for example, the ammonium salts, quaternary ammonium salts, the alkali and earth alkaline metal salts, e.g. the lithium, sodium, potassium, magnesium, calcium salts and the like, salts with organic bases, e.g. the benzathine, N-methyl, -D-glucamine, hydrabamine salts, and salts with amino acids such as, for example, arginine, lysine and the like.

Conversely said base addition salt forms can be converted by treatment with an appropriate acid into the free acid form.

The term "salts" also comprises the hydrates and the solvent addition forms that the prodrug compounds of the present invention are able to form. Examples of such forms are e.g. hydrates, alcoholates and the like. The term "salts" also comprises the quaternization of the nitrogen atoms of the present compounds.

A basic nitrogen can be quaternized with any agent known to those of ordinary skill in the art including, for instance, lower alkyl halides, dialkyl sulfates, long chain halides and arylalkyl halides.

The present prodrug compounds may also exist in their tautomeric forms. Such forms, although not explicitly indicated in the above formula, are intended to be included within the scope of the present invention.

In one embodiment, the terminal amino group of the terminal amino acid of the peptide bond formed by —(Y—X)$_n$ may optionally contain one or two capping groups selected from acetyl, succinyl, benzyloxycarbonyl, glutaryl, morpholinocarbonyl and $C_{1-4}$alkyl.

In one embodiment, each X independently is selected from a naturally occurring amino acid.

In one embodiment, each X independently is an L-amino acid selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine.

In one embodiment, each Y independently is proline, alanine, glycine, serine, valine or leucine; preferably each Y independently is proline or alanine.

In one embodiment, n is 1, 2 or 3.

In one embodiment, $R^1$ is heterocycloalkyloxy, heteroaryl, heteroarylC1-4alkyloxy, aryl or aryloxyC-4alkyl.

In one embodiment, $R^1$ is hexahydrofuro [2,3-b]furanyl-oxy, tetrahydrofuranyl-oxy, quinolinyl, thiazolylmethyloxy, aryl, aryloxymethyl.

In one embodiment, $R^1$ is hexahydrofuro [2,3-b]furan-3-yl-oxy, tetrahydrofuran-3-yl-oxy, quinolin-2-yl, thiazol-5-ylmethyloxy, 3-hydroxy-2-methyl-1-phenyl, 2,6-dimethylphenoxymethyl.

In one embodiment, $R^1$ is (3R,3aS,6aR)-hexahydrofuro [2,3-b]furan-3-yl-oxy, (3S)-tetrahydrofuran-3-yl-oxy, quinolin-2-yl, thiazol-5-ylmethyloxy, 3-hydroxy-2-methyl-1-phenyl, 2,6-dimethylphenoxymethyl.

Interesting groups of compounds are those groups of compounds of formula (I) thereof where one or more of the following restrictions apply:
n is 1, 2 or 3;
Y is proline;
each X independently is selected from valine, aspartic acid, lysine or proline;
Z is methylene;
$R^1$ is heterocycloalkyloxy;
$R^2$ is phenylmethyl;
$R^3$ is $C_{1-10}$alkyl;
$R^4$ is hydrogen.

Interesting compounds are those compounds of formula (I) or any defined subgroup thereof wherein $R^2$ is phenylmethyl.

Interesting compounds are those compounds of formula (I) or any defined subgroup thereof wherein $R^3$ is $C_{1-4}$alkyl, in particular $R^3$ is isobutyl.

Interesting compounds are those compounds of formula (I) or any defined subgroup thereof wherein $R^4$ is hydrogen.

Interesting compounds are those compounds of formula (I) or any defined subgroup thereof wherein $R^2$ is phenylmethyl; $R^3$ is isobutyl and $R^4$ is hydrogen.

Interesting compounds are those compounds of formula (I) or any defined subgroup thereof wherein $Z^4$ is methylene.

Interesting compounds are those compounds of formula (I) or any defined subgroup thereof wherein $R^1$ is hexahydrofuro [2,3-b]furanyl-oxy, tetrahydrofuranyl-oxy, quinolinyl, thiazolylmethyloxy, aryl, aryloxymethyl; $R^2$ is phenylmethyl; $R^3$ is isobutyl and $R^4$ is hydrogen.

A particular group of compounds are those compounds of formula (I) or any defined subgroup thereof wherein
n is 1, 2 or 3;
Y is proline or alanine;
each X independently is selected from a naturally occurring amino acid;
Z is a direct bond or methylene;
$R^1$ is heterocycloalkyloxy, heteroaryl, heteroaryl$C_{1-4}$alkyloxy, aryl or aryloxy$C_{1-4}$alkyl;
$R^2$ is phenylmethyl;
$R^3$ is isobutyl; $R^4$ is hydrogen.

Also a particular group of compounds are those compounds of formula (I) or any defined subgroup thereof wherein
n is 1, 2 or 3;
Y is proline;
each X independently is selected from a naturally occurring amino acid;
Z is methylene;
$R^1$ is hexahydrofuro [2,3-b]furanyl-oxy, tetrahydrofuranyl-oxy, quinolinyl, thiazolylmethyloxy, aryl, aryloxymethyl;
$R^2$ is phenylmethyl;
$R^3$ is isobutyl;
$R^4$ is hydrogen.

The compounds of formula (I) are prodrugs for the therapeutic compounds of formula (Ia)

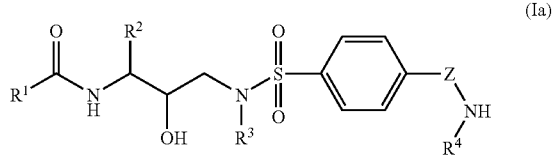

(Ia)

wherein $R^1$, $R^2$, $R^3$, $R^4$ and Z are as defined in the compounds of formula (I) and the different embodiments.

These therapeutic compounds of formula (Ia) are known to have HIV protease inhibiting activity and are described in EP656887, EP715618, EP810209, U.S. Pat. No. 5,744,481, U.S. Pat. No. 5,786,483, U.S. Pat. No. 5,830,897, U.S. Pat.

No. 5,843,946, U.S. Pat. No. 5,968,942, U.S. Pat. No. 6,046,190, U.S. Pat. No. 6,060,476, U.S. Pat. No. 6,248,775, WO99/67417 all incorporated herein by reference.

Due to the fact that some therapeutic compounds are inhibitors of the replication of HIV, the prodrug compounds of said therapeutic compounds are useful in the treatment of warm-blooded animals, in particular humans, infected with HIV. Conditions associated with HIV which may be prevented or treated with the compounds of the present invention include AIDS, AIDS-related complex (ARC), progressive generalized lymphadenopathy (PGL), as well as chronic CNS diseases caused by retroviruses, such as, for example HIV mediated dementia and multiple sclerosis.

The prodrug compounds of anti-HIV therapeutic compounds of the present invention may therefore be used as medicines against or in a method of treating above-mentioned conditions. Said use as a medicine or method of treatment comprises the systemic administration of an effective therapeutic amount of a anti-HIV therapeutic compound to HIV-infected warm-blooded animals, in particular HIV-infected humans. Consequently, the prodrug compounds of the present invention can be used in the manufacture of a medicament useful for treating conditions associated with HIV infection.

The term stereochemically isomeric forms of compounds of the present invention, as used hereinbefore, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 80% of one isomer and maximum 20% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess and the diastereomeric excess respectively, of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of the compounds of the present invention can be obtained separately by conventional methods. Appropriate physical separation methods which may advantageously be employed are, for example, selective crystallization and chromatography, e.g. column chromatography.

The compounds may contain one or more asymmetric centers and thus may exist as different stereoisomeric forms. The absolute configuration of each asymmetric center that may be present in the compounds may be indicated by the stereochemical descriptors R and S, this R and S notation corresponding to the rules described in Pure Appl. Chem. 1976, 45, 11-30.

The present invention is also intended to include all isotopes of atoms occurring on the present compounds of the invention. Isotopes include those atoms having the same atomic number but different mass numbers. By way of general example and without limitation, isotopes of hydrogen include tritium and deuterium. Isotopes of carbon include C-13 and C-14.

In general, the therapeutic compounds of formula (Ia) can be prepared as described in EP656887, EP715618, EP810209, U.S. Pat. No. 5,744,481, U.S. Pat. No. 5,786,483, U.S. Pat. No. 5,830,897, U.S. Pat. No. 5,843,946, U.S. Pat. No. 5,968,942, U.S. Pat. No. 6,046,190, U.S. Pat. No. 6,060,476, U.S. Pat. No. 6,248,775, WO99/67417.

The prodrug compounds of formula (I) can be prepared starting from the therapeutic compounds of formula (Ia) using art-known peptide chemistry.

Scheme 1

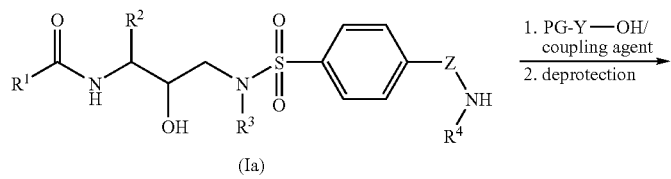

(Ia)

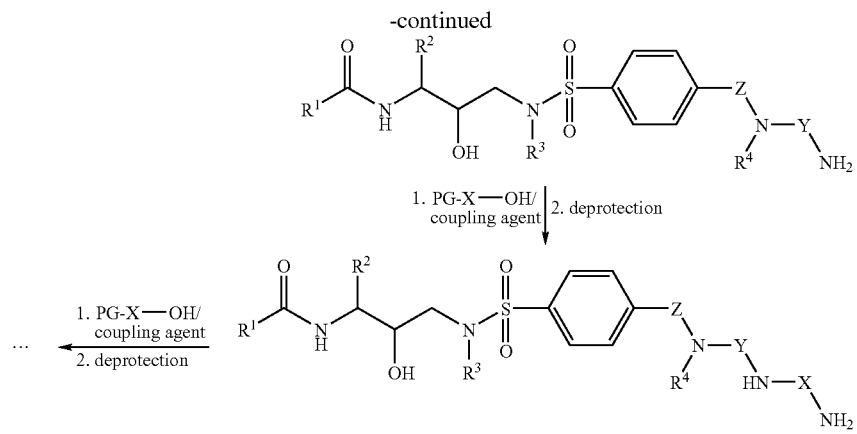

For instance, amino acids may be coupled to the therapeutic compound D to form peptide bonds as depicted in scheme 1. This coupling reaction may be performed in an appropriate reaction-inert solvent such as N,N-dimethylformamide, acetonitrile, dichloromethane, tetrahydrofuran or any other solvent that solubilizes the reagents, with an amino protected amino acid of formula PG-Y—OH wherein PG (protecting group) may be for instance a Boc (tert-butyl oxycarbonyl), Cbz (benzyloxycarbonyl) or Fmoc, in the presence of a coupling agent such as DCC (dicyclohexylcarbodiimide) or EDCI (1-(3-dimethylaminopropyl)-3-ethylcarbodiimide hydrochloride) and HOAt (1-hydroxy-7-azabenzotriazol) or a functional equivalent thereof. The thus formed peptide may then be deprotected using conventional deprotection techniques such as for instance deprotection with trifluoroacetic acid in dichloromethane.

This coupling and subsequent deprotection reaction step can be repeated using PG-X—OH as reagent to form the desired peptide bond.

Some of the amino acids, such as for example lysine and aspartic acid may require a second protecting group and can be represented in formula PG-(XPG)-OH or PG-(YPG)-OH.

Alternatively, a reagent of formula PG-X—Y—OH, or PG-(X)$_n$—OH, or PG-(X)$_n$—Y—OH, or PG-(X—Y)$_n$ can be used in the above reaction procedures.

In preparations presented above, the reaction products may be isolated from the reaction medium and, if necessary, further purified according to methodologies generally known in the art such as, for example, extraction, crystallization, distillation, trituration and chromatography.

The compounds of the invention as prepared in the hereinabove described processes may be synthesized as a mixture of stereoisomeric forms, in particular in the form of racemic mixtures of enantiomers which can be separated from one another following art-known resolution procedures. The racemic compounds of the invention may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of the invention involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of the present invention can thus be used in animals, preferably in mammals, and in particular in humans as pharmaceuticals per se, in mixtures with one another or in the form of pharmaceutical preparations.

In another aspect the invention provides a method of detecting dipeptidyl-peptidase producing tissue or cells by using the prodrug technology of the invention, as described above. The method is carried out by contacting a detectably labeled peptide of the invention with target tissue for a period of time sufficient to allow a dipeptidyl-peptidase such as CD26 to cleave the peptide and release the detectable label. The detectable label is then detected. The level of detection is then compared to that of a control sample not contacted with the target tissue. Many varieties of detectable label are available, including optically based labels, such as chromophoric, chemiluminescent, fluorescent or phosphorescent labels, and radioactive labels, such as alpha, beta or gamma emitting labels. Examples of fluorescent labels include amine-containing coumarins such as 7-amino-4-methylcoumarin, 7-amino-4-trifluoromethyl, and other amine-containing fluorophores such as 6-aminoquinoline, 2-aminopurines, and rhodamines, including rhodamine 110. Examples of radioactive labels include beta emitters such as $^3$H, $^{14}$C and $^{125}$I. Examples of chromophoric labels (those that have characteristic absorption spectra) include nitroaromatic compounds such as p-nitroaniline. Examples of chemiluminescent labels include luciferins such as 6-amino-6-deoxyluciferin.

Preferably, the choice of detectable label allows for rapid detection and easily interpretable determinations. Detectable labels for use in the invention preferably show clearly detectable differences between detection from the cleaved and uncleaved state.

The invention provides a method for detecting a disorder accompanied with overexpression or lowered expression of dipeptidyl-peptidases, more preferably CD26, which comprises contacting a prodrug with a cell suspected of having a dipeptidyl-peptidase-production associated disorder and detecting cleavage of the peptide. The peptide reactive with dipeptidyl-peptidase is labeled with a compound which allows detection of cleavage by dipeptidyl-peptidase. For purposes of the invention, a prodrug may be used to detect the level of enzymatically active dipeptidyl-peptidase in biological fluids and tissues such as saliva, blood, or urine. The level of dipeptidyl-peptidase in the suspected cell can be compared with the level in a normal cell to determine whether the subject has a dipeptidyl-peptidase-production associated cell disorder.

The invention also provides a method of selecting potential prodrugs for use in the invention. The method generally consists of contacting prodrugs of the invention with dipeptidyl-peptidases, such as CD26 or tissue or cells producing these dipeptidyl-peptidases and with dipeptidyl-peptidases free medium in a parallel experiment.

In a certain embodiment of the invention, the above described prodrugs can be used as a medicine. In another embodiment, the above described prodrugs can be used to manufacture a medicament to prevent or to treat a certain disease. The disease that will be treated depends on the therapeutical drug that will be used in the prodrug technology.

The invention furthermore provides methods of treating a certain disease by administering a prodrug as described by the invention. The prodrugs of the invention and/or analogs or derivatives thereof can be administered to any host, including a human, a non-human animal and mammals, in an amount effective to treat a disorder.

To further optimise the pharmacokinetic profile of the prodrugs of present invention they can be administered in conjunction with a suitable delivery vehicle (e.g., microcapsules, microspheres, biodegradable polymer films, lipid-based delivery systems such as liposomes and lipid foams, viscous instillates and absorbable mechanical barriers) useful for maintaining the necessary concentrations of the prodrugs or the therapeutic compound D at the site of the disease.

The prodrug or "medicament" may be administered by any suitable method within the knowledge of the skilled man. Modes of administration known in the art for therapeutic agents include parenteral, for example, intravenous (e.g. for antibody inhibitors), intraperitoneal, intramuscular, intradermal, and epidermal including subcutaneous and intradermal, oral, or application to mucosal surfaces, e.g. by intranasal administration using inhalation of aerosol suspensions, and by implanting to muscle or other tissue in the subject. Suppositories and topical, locally applied preparations are also contemplated. Depending on the route and place of administration, more hydrophobic or hydrophilic peptide moieties of the prodrug can be considered.

In the present invention, the prodrugs are introduced in amounts sufficient to prevent, reduce or treat a certain disease, depending on the administration route.

The most effective mode of administration and dosage regimen for the prodrugs or the "medicament" in the methods of the present invention depend on the severity of the disease to be treated, the subject's health, previous medical history, age, weight, height, sex and response to treatment and the judgement of the treating physician. Therefore, the amount of prodrug to be administered, as well as the number and timing of subsequent administrations are determined by a medical professional conducting therapy based on the response of the individual subject. Initially, such parameters are readily determined by skilled practitioners using appropriate testing in animal models for safety and efficacy, and in human subjects during clinical trials of prodrug formulations. After administration, the efficacy of the therapy using the prodrugs is assessed by various methods including assessment of the clinical picture.

Suitable pharmaceutical carriers for use in said pharmaceutical compositions and their formulation are well known to those skilled in the art, and there is no particular restriction to their selection within the present invention. Suitable carriers or excipients known to the skilled man are saline, Ringer's solution, dextrose solution, Hank's solution, fixed oils, ethyl oleate, 5% dextrose in saline, substances that enhance isotonicity (such as sugars or sodium chloride) and chemical stability, buffers and preservatives. Other suitable carriers include any carrier that does not itself induce the production of antibodies harmful to the individual receiving the composition such as proteins, polysaccharides, polylactic acids, polyglycolic acids, polymeric amino acids and amino acid copolymers. They may also include additives such as wetting agents, dispersing agents, stickers, adhesives, emulsifying agents, solvents, coatings, antibacterial and antifungal agents (for example phenol, sorbic acid, chlorobutanol) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents may also be prepared by inicronisation, for instance in view to obtain them in the form of microspheres usually having a diameter of about 1 to 10 um, namely for the manufacture of microcapsules for controlled or sustained release of the active ingredients.

Suitable surface-active agents to be used in the pharmaceutical compositions of the present invention are non-ionic, cationic and/or anionic materials having good emulsifying, dispersing and/or wetting properties.

Suitable anionic surfactants include both water-soluble soaps and water-soluble synthetic surface-active agents. Suitable soaps are alkaline or alkaline-earth metal salts, unsubstituted or substituted ammonium salts of higher fatty acids (C10-C22), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcanolamine salts of dodecylbenzene sulphonic acid or dibutyl-naphthalenesulphonic acid or a naphthalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidyl-choline, dipalmitoylphoshatidyl-choline and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, preferably halides, having 4 hydrocarbon radicals optionally substituted with halo, phenyl, substituted phenyl or hydroxy; for instance quaternary ammonium salts containing as N-substituent at least one $C8C_{2-2}$ alkyl radical (e.g. cetyl, lauryl, palmityl, myristyl, oleyl and the like) and, as further substituents, unsubstituted or halogenated lower alkyl, benzyl and/or hydroxy-lower alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbuch', 2 d ed. (Hanser Verlag, Vienna, 1981) and "Encyclopaedia of Surfactants, (Chemical Publishing Co., New York, 1981).

Additional ingredients may be included in order to control the duration of action of the active ingredient in the composition. Control release compositions may thus be achieved by selecting appropriate polymer carriers such as for example polyesters, polyamino acids, polyvinyl pyrrolidone, ethylene-vinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethylcellulose, polymethyl methacrylate and the other above-described polymers.

Such methods include colloid drug delivery systems like liposomes, microspheres, microemulsions, nanoparticles, nanocapsules and so on. Depending on the route of administration, the pharmaceutical composition may require protective coatings. Pharmaceutical forms suitable for injectionable use include sterile aqueous solutions or non-aqueous solutions or dispersions (suspensions, emulsions) and sterile powders for the extemporaneous preparation thereof. Typical carriers for this purpose therefore include biocompatible aqueous buffers, ethanol, glycerol, propylene glycol, polyethylene glycol, vegetable oils such as olive oil, and injectable organic esters such as ethyl oleate and the like and mixtures thereof. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, cheating agents, and inert gases, and the like.

The present invention thus provides in a preferred embodiment di- and oligopeptidyl derivatives of drugs that act as efficient substrates for dipeptidyl-peptidases present on the surface of cells or in plasma. By linking for example water-insoluble, lipophilic drugs to (polar) di- or oligopeptides, these drugs become more water-soluble in biological fluids and physiological media, but may also gain (oral) bioavailability due to specific recognition by the intestinal hPEPT-1 and related peptide transporters. Valine derivatives of nucleoside analogues such as valacyclovir and valganciclovir are examples of nucleoside prodrugs that are substrate for hPEPT-1, and whose solubility, absorption and systemic availability has been markedly improved compared with the parent compounds due to intestinal epithelial brush-border membrane peptide-carrier-mediated transport. Thus, according to one embodiment of the invention the prodrugs of the present invention are CD26 cleavable prodrugs having a dipeptide or tetrapeptide with valine at the aminoterminal position or are CD26 cleavable prodrugs having a tetrapeptide wherein the first and/or the third amino acid is a valine. Modifying the number and nature of the amino acids in the (oligo) peptide part influences the dipeptidyl-peptidase (such as CD26) susceptibility of the prodrug molecule, but also the degree of aqueous solubility, plasma protein binding and bioavailability, as well as plasma half-life. The amino acid composition can be optimized in function of the nature and biological application of the particular drug.

Dipeptidyl peptidase requires a free amino group on the aminoterminus of the peptide and requires an L configuration of the amino acids in the peptide to be cleaved of. Unmodified dipeptides with L amino acids have a low toxicity compared with other groups being used in the art for the generation of prodrugs. Thus according to an embodiment, the prodrugs of the present invention allow the generation of prodrugs with lowered side effects upon release of the protecting dipeptidyl group.

The invention will be further described in the following examples, which do not limit the scope of the invention described in the claims.

EXAMPLES

TSAO Prodrugs

Example 1

Conversion of Val-Pro-NAP-TSAO and Val-Pro-Val-NAP-TSAO to the Parent Compounds NAP-TSAO and Val-NAP-TSAO by Purified CD26

Figure 2:
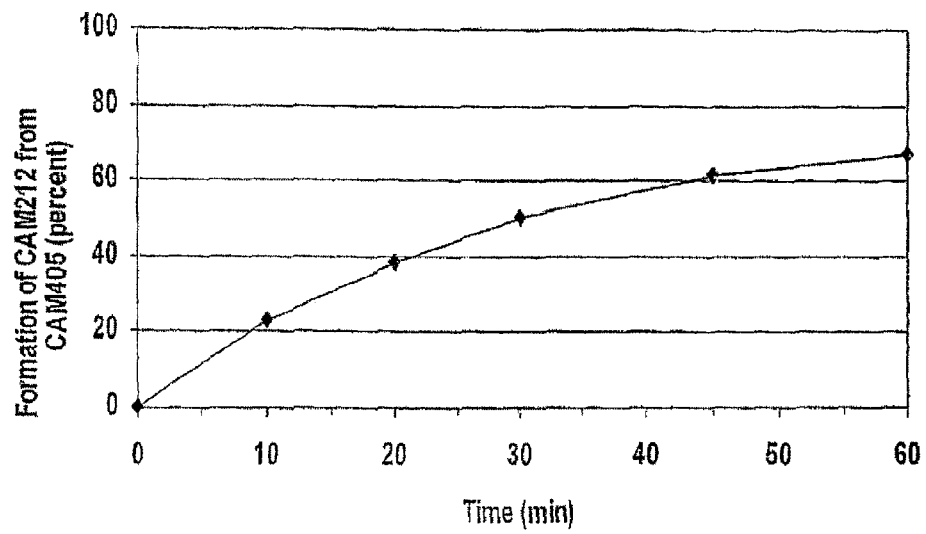
FIG. 2 shows, according to one embodiment of the invention, the conversion of 50 μM Val-Pro-NAP-TSAO (CAM-405) to NAP-TSAO (CAM-212) by purified CD26 (5.7 mUnits) in function of incubation time (37° C.).
Figure 3:
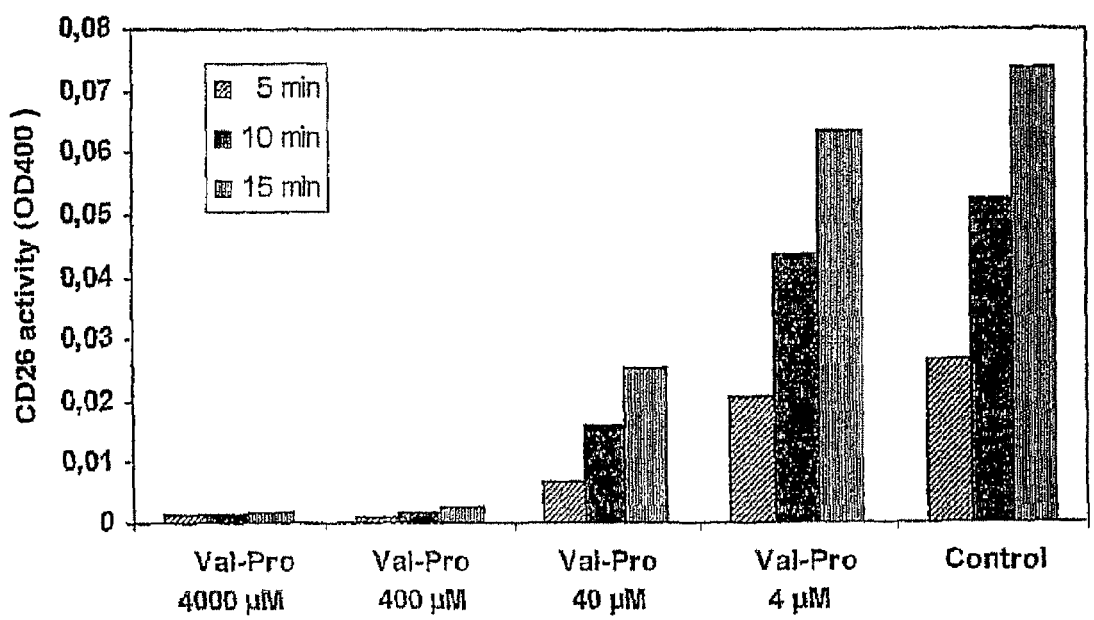
FIG. 3 shows the inhibitory effect of different concentrations of the dipeptide Val-Pro against CD26-catalysed conversion of the chromophoric substrate GP-pNA (25 μM) to GP+pNA at 5 (left bar), 10 (middle bar) or 15 min (right bar) of reaction. The CD26 catalytic reaction was measured by recording the increase of absorption caused by pNA release at 400 nm.

The lipophilic $N^3$-aminopropyl-substituted TSAO-$m^3$T nucleoside derivative NAP-TSAO (CAM-212) has been chemically linked to the dipeptide Val-Pro and the tripeptide Val-Pro-Val through the free carboxylic acid end of the di/tripeptide resulting in CAM-405 (Val-Pro-NAP-TSAO) and CAM-431 (Val-Pro-Val-NAP-TSAO) (FIG. 1). To reveal whether CD26 recognizes such synthetic di/tripeptide derivatives of lipophilic nucleoside analogues as a substrate, 50 µM CAM-405 or CAM-431 was exposed to 5.7 mUnits of purified CD26, and the conversion of CAM-405 or CAM-431 to respectively CAM-212 or CAM-403 (Val-NAP-TSAO) was recorded in function of incubation time by HPLC analysis. The identity of the formed CAM-212 product was revealed by HPLC analysis using the reference parent compound as control, and by mass spectrometry. We found that CD26 efficiently removed the dipeptide Val-Pro from CAM-405 resulting in the time-dependent appearance of the parent compound CAM-212 (FIG. 2). Within the first 10 min of the reaction, at least 20% of CAM-405 had been converted to CAM-212, fifty percent of the TSAO dipeptide derivative was converted to CAM-212 within 30 min of the reaction and ~67% of CAM-405 was hydrolyse after 60 min. Thus, the reaction rate started already to slow down after the first 10 min of drug exposure (FIG. 2). Most likely, the release of the reaction product Val-Pro dose-dependently feed-back inhibited the CD26-catalysed dipeptidyl-peptidase reaction. Similar data were obtained for the conversion of the tripeptide derivative Val-Pro-Val-NAP-TSAO (CAM-431) to the Val-NAP-TSAO product (CAM-403) (data not shown). When the dipeptide Val-Pro was evaluated for its inhibitory effect against CD26, 4 mM completely inhibited the reaction; 400 µM Val-Pro inhibited the reaction by >>90%, whereas 40 µM and 4 µM prevented CD26-catalysed p-nitroaniline release from GP-pNA by 70 and 15%, respectively (FIG. 3). Thus, in the presence of 50 µM CAM-405, hydrolysis of 50% of CAM-405 to CAM-212 results in the appearance of 25 µM Val-Pro, that is a concentration that (feed-back) inhibits the CD26 reaction by ~50%. These findings explain why the CD26-catalysed reaction levels-off shortly after the start of the exposure of the drug to CD26. In contrast, the dipeptide Lys-Pro could be completely removed from Lys-Pro-NAP-TSAO by CD26, pointing to a lack of feed-back inhibition of CD26 by free Lys-Pro. Thus, a further level of modulation of the rate of prodrug release can be introduced by choosing a dipeptide moiety that competes for the active site of CD26, until the dipeptide has diffused from the tissue wherein CD26 is present. The inhibitory activity of any dipeptide can be evaluated by the above mentioned assay.

The conversion rate in function of time is given in Table 1 for NAP-TSAO-dipeptides where the dipeptide consists of: Val-Pro, Val-D-Pro, Asp-Pro, Lys-Pro, Tyr-Pro, Gly-Pro, Val-4-hydroxyPro, Gly-3,4-dihydroxyPro, but also Val-Gly, Val-Ala, Val-Leu and Val-Phe. It is clear that the conversion rate to the parent NAP-TSAO differs depending the nature of the dipeptide. Also, when the terminal amine of the dipeptide has been blocked by a lipophilic group (i.e. methyl, Z or Fmoc), the prodrug looses measurable substrate activity for CD26.

TABLE 1

Dipeptide prodrugs: conversion rate to parent compound by purified CD26 (1.5 mUnits)

| CAM-nr | Product | RT(min) | Conversion % | | |
|---|---|---|---|---|---|
| | | | 1 h | 4 h | 24 h |
| 405 | H-Val-Pro-NAP-TSAO | 29.4 | 37 | 62 | 61 |
| 404 | Z-Val-NAP-TSAO | 38.9(*) | 0 | 0 | 0 |
| 163 | H-Val-4HyPro-NAP-TSAO | 27.59 | 4.1 | 18 | 53 |
| 462 | NH$_2$-Val-HyPro(Bzl)-NAP-TSAO | 41.7(*) | — | 0 | 0 |
| 465 | H-Gly-3.4Hypro-NAP-TSAO | 26.34 | | 0 | 0 |
| 430 | H-Val-D-Pro-NAP-TSAO | 31.56 | 0 | ~1 | ~2 |
| 437 | H-Lys-Pro-NAP-TSAO | 23.33 | — | 85 | 99 |
| 458 | H-Gly-Pro-NAP-TSAO | 27.7 | 5 | 20 | 58 |
| 456 | H-Tyr-Pro-NAP-TSAO | 30.6 | 43 | 66 | 79 |
| 435 | H-Asp-Pro-NAP-TSAO | 25.49 | — | 7.9 | 30 |
| 424 | H-Val-Ala-NAP-TSAO | 28.86 | 0 | 6.5 | 35 |
| 422 | H-Val-Gly-NAP-TSAO | 28.56 | 0 | 0 | 0 |
| 426 | H-Val-Leu-NAP-TSAO | 33.55 | 0 | 0 | 0 |
| 428 | H-Val-Phe-NAP-TSAO | 34.6 | 0 | 0 | 0 |
| 431 | H-Val-Pro-Val-NAP-TSAO | 31.07 | — | 51 | ~70 |
| 411 | H-Val-Pro-Val-NHP-TSAO | 35.3 | 33 | 60 | — |
| 407 | Me-NH-Val-Pro-Val-NHP-TSAO | | 0 | 0 | 0 |

Rt(min): retention time (*)refers to retention time obtained with an extended gradient comprising after 30 min.: increase form 50% to 90% acetonitrille during 10 min, and remaining 90% acetonitrille for another 10 min.

Example 2

Conversion of tetrapeptide-NAP-TSAO Compounds to the Parent Compound NAP-TSAO by Purified Human CD26

The conversion rate in function of time is given in Table 2 for tetrapeptide NAP-TSAO compounds where the tetrapeptide consists of: Val-Pro-Val-Pro [SEQ ID no:6] (CAM 467), Val-Ala-Val-Pro [SEQ ID no:7] (CAM 473) or Lys-Pro-Asp-Pro [SEQ ID no:8] (CAM 477). It is clear that the conversion rate to the parent NAP-TSAO of CAM 473 occurs faster than with the Val-Ala-NAP-TSAO (CAM 424). Only traces of dipeptide prodrug (CAM 405) is seen as intermediate in the conversion of the tetrapeptide CAM 473 to NAP-TSAO. Also Val-Pro-Val-Pro-NAP-TSAO [SEQ ID NO:6] is quickly converted to NAP-TSAO. In contrast, CAM 477 conversion to NAP-TSAO clearly occurs in two steps, the fast initial step forming CAM 435 (Asp-Pro-NAP-TSAO) followed by the slow second step forming eventually NAP-TSAO (CAM 212) from Asp-Pro-NAP-TSAO.

TABLE 2

Tetrapeptide prodrugs: conversion rate to parent compound by purified CD26 (1.5 mUnits)

| CAM-nr | Product | RT(min) | % conversion | | |
|---|---|---|---|---|---|
| | | | 1 h | 4 h | 24 h |
| 405 | H-Val-Pro-NAP-TSAO | 29.4 | 37 | 62 | 61 |
| 424 | H-Val-Ala-NAP-TSAO | 28.86 | 0 | 6.5 | 35 |
| 435 | H-Asp-Pro-NAP-TSAO | 25.49 | — | 7.9 | 30 |
| 437 | H-Lys-Pro-NAP-TSAO | 23.33 | — | 85 | 99 |
| 466 | Z-Val-Pro-Val-Pro-NAP-TSAO [SEQ ID no: 9] | 39.3(*) | 0 | 0 | 0 |
| 467 | H-Val-Pro-Val-Pro-NAP-TSAO [SEQ ID no: 6] | 30.5 | 43 | 86 | 88 |
| 473 | H-Val-Ala-Val-Pro-NAP-TSAO [SEQ ID no: 7] | 30.19 | 12 | 54 | 70 |
| 477 | H-Lys-Pro-Asp-Pro-NAP-TSAO [SEQ ID no: 8] | 22.63 | 88$^a$/2.1$^b$ | 86$^a$/6.0$^b$ | 74$^a$/26$^b$ |

$^a$dipeptide intermediate
$^b$parent compound (*)refers to retention time obtained with an extended gradient comprising after 30 min.: increase from 50% to 90% acetonitrille during 10 min, and keep 90% acetonitrille for another 10 min.

Example 3

Figure 4:
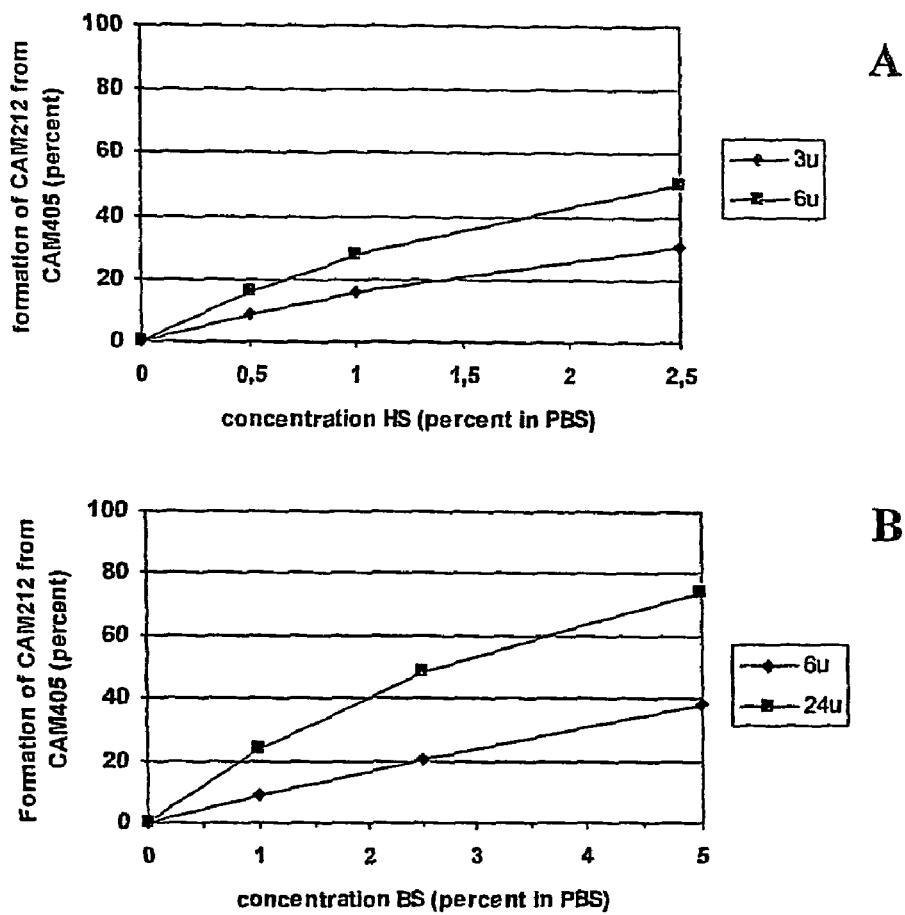
FIG. 4 shows, according to one embodiment of the invention, the conversion of 50 μM Val-Pro-NAP-TSAO (CAM-405) to NAP-TSAO (CAM-212) in several dilutions of human serum (HS) (FIG. 4A) and bovine serum (BS) (FIG. 4B) in PBS. Conversion was recorded after 3, 6 or 24 hrs of incubation.

Conversion of Val-Pro-NAP-TSAO and Val-Pro-Val-NAP-TSAO to the Parent Compounds NAP-TSAO and Val-NAP-TSAO by Human and Bovine Serum Human and bovine serum were incubated for 3 hr, 6 hr and/or 24 hr at 37° C. in the presence of 50 μM CAM-405. The sera were diluted in PBS at a final concentration of 0.5, 1, 2.5 or 5%. Both human (HS) and bovine (BS) serum efficiently converted CAM-405 to CAM-212. The longer the incubation time, and the higher the serum concentration used, the faster the conversion of CAM-405 to CAM-212 occurred (FIG. 4). As also noted for CD26, HS- and BS-catalysed reaction slowed down in function of time, and was not linearly proportional with serum concentration (FIG. 4). These findings provide again evidence for a pronounced feed-back inhibition of dipeptidyl-peptidase activity in human and bovine serum by the released Val-Pro dipeptide. HS was more efficient in converting CAM-405 to CAM-212 than BS (FIG. 4). Since 1% HS is able to hydrolyse ~20% of 50 μM CAM-405 within 3 hrs of incubation, it could be calculated that undiluted serum would have been able to convert this prodrug amount to its parent compound at a hundred fold higher speed, that is, within 1.8 min, provided that no feed-back inhibition would have occurred (as expected in the intact organism where release of Pro-Val would immediately result in disappearance from the plasma due to several mechanisms including organ uptake, renal excretion, etc.). This means that 10 μM CAM-405 should have a half-life of less than 1.8 min in plasma, and thus, will virtually immediately be converted to its parental drug as soon as it appears in the plasma.

Example 4

Conversion of Val-Pro-NAP-TSAO to the Parent Compound NAP-TSAO by CEM Cell Suspensions The conversion of Val-Pro-NAP-TSAO (CAM-405) to NAP-TSAO (CAM-212) also efficiently occurred by carefully washed T-lymphocytic CEM cell suspensions in PBS. Ten million CEM cells suspended in 200 μl PBS hydrolysed the Val-Pro moiety from CAM-405 by 65% within 3 hrs of incubation at 37° C. This amount of hydrolysis was found both in the PBS supernatant and in the CEM cell extracts. Presumably, CD26 present in the cell membrane of CEM cells had cleaved-off the Val-Pro from CAM-405 after which both truncated and intact prodrug had been taken up by the lymphocytic cells to an equal extent.

Example 5

Figure 5:
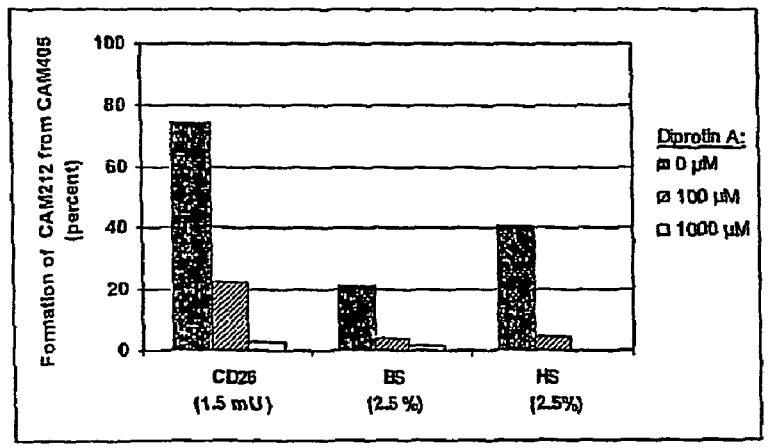
FIG. 5 shows the inhibitory effect of Diprotin A on the conversion of 50 μM Val-Pro-NAP-TSAO (CAM-405) to NAP-TSAO (CAM-212) by purified CD26 (1.5 mUnits), 2.5% bovine serum (BS) in PBS or 2.5% human serum (HS) in PBS. (Left bar: 0 μM; middle bar: 100 μM; right bar: 1000 μM)

Effect of Specific CD26 Inhibitors on the Conversion of Val-Pro-NAP-TSAO to NAP-TSAO CD26-catalysed CAM-405 conversion to CAM-212 was recorded in the absence or presence of the CD26 inhibitor diprotin A (FIG. 5). Interestingly, at the highest concentration of the inhibitors (1000 μM), a nearly complete prevention of the conversion of CAM-405 to CAM-212 occurred in both HS and BS or by purified CD26. At 10-fold lower inhibitory concentrations (i.e. 100 μM) diprotin A still efficiently suppressed (>>50%) the CD26-catalysed conversion of CAM-405 to CAM-212 by purified CD26 preparations and by HS and BS (FIG. 5). These observations point to CD26 as the main and predominant enzyme responsible in HS and BS to remove the dipeptide part from the lipophilic NAP-TSAO dipeptide nucleoside analogue.

Example 6

Hydrolysis of Dipeptide Prodrugs in the Presence of Purified CD26 and Human Serum A variety of different NAP-TSAO dipeptide and tripeptide derivatives were synthesized and evaluated for their ability to act as an efficient substrate for CD26. CAM-431 (Val-Pro-Val-NAP-TSAO), containing a tripeptide (Val-Pro-Val) moiety linked to NAP-TSAO was also hydrolyse by CD26, releasing the dipeptide Val-Pro and the remaining valine-substituted Val-NAP-TSAO. Interestingly, CAM-407 (CH3-Val-Pro-Val-TSAO) containing a methyl group at the free amino group of Val in CAM-412 completely lacked substrate activity for CD26. Even after 24 hrs of incubation, no traces of a formed truncated CH3-Val-Pro-Val-NAP-TSAO derivative could be observed. Similar observations were made for Val-Pro-NAP-TSAO or Val-Pro-Val-NAP-TSAO derivatives at which a lipophilic entity was linked on the free amino group of valine. Thus, a free amino group on the ultimate amino acid is a prerequisite for substrate activity by CD26. In addition to Val-Pro, we also found Lys-Pro a very efficient dipeptide to be cleaved by CD26. Asp-Pro was much less efficiently cleaved.

When the dipeptide Val-Pro on NAP-TSAO was replaced by other dipeptides such as Val-Gly, Val-Leu or Val-Phe, no CD26-catalysed conversion to the parent compound was observed, even after 24 hrs of incubation. Also, when L-Pro in Val-Pro-NAP-TSAO was replaced by D-Pro, the compound did not act anymore as a good substrate for purified CD26, and Val-(D) Pro was practically not split-off. However, Val-Ala linked to NAP-TSAO, was the only alternative dipeptide found, together with Val-Pro, that was efficiently released from the parent NAP-TSAO molecule by CD26. Thus, as with natural peptides that contain a penultimate Pro or Ala at their $NH_2$ terminal, CD26 is also able to recognize this dipeptide sequence when linked through an amide binding to a molecule (i.e. TSAO) different from a peptide.

Figure 6:
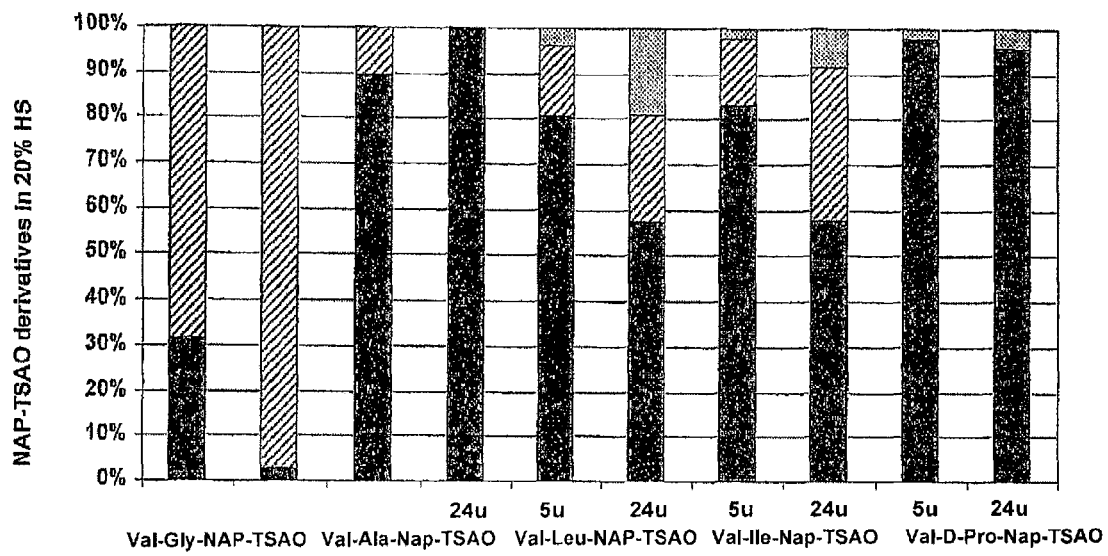
FIG. 6 shows the conversion of a variety of dipeptide derivatives of NAP-TSAO (50 μM) by 20% human serum in PBS in function of incubation time. Black bars (bottom part) represent the parent dipeptide derivatives of NAP-TSAO. Grey bars (middle part) represent NAP-TSAO-amino acyl derivatives from which the last amino acid (valine) has been removed. White bars (top part) represent NAP-TSAO (CAM-212) that had been released from the dipeptidyl-NAP-TSAO derivatives.
Figure 7:
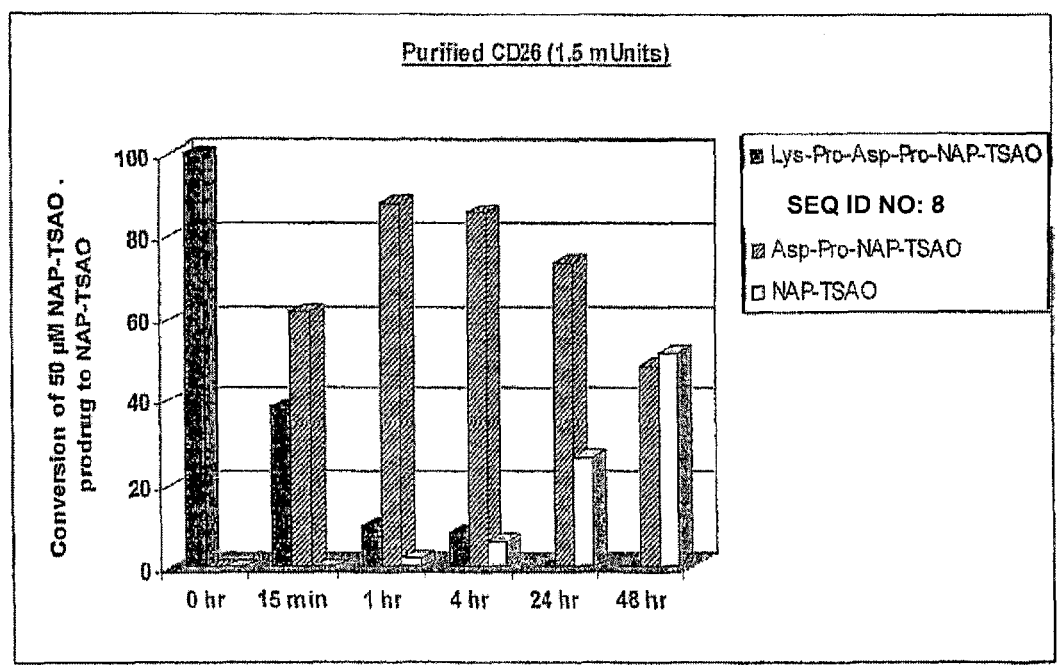
FIG. 7 shows the conversion of the tetrapeptide Lys-Pro-Asp-Pro-NAP-TSAO [SEQ ID NO:8] to NAP-TSAO. Formation of the dipeptide (Asp-Pro)-NAP-TSAO intermediate is clearly formed and later on further converted to the parent drug. This shows a 2-step reaction.
Figure 8:
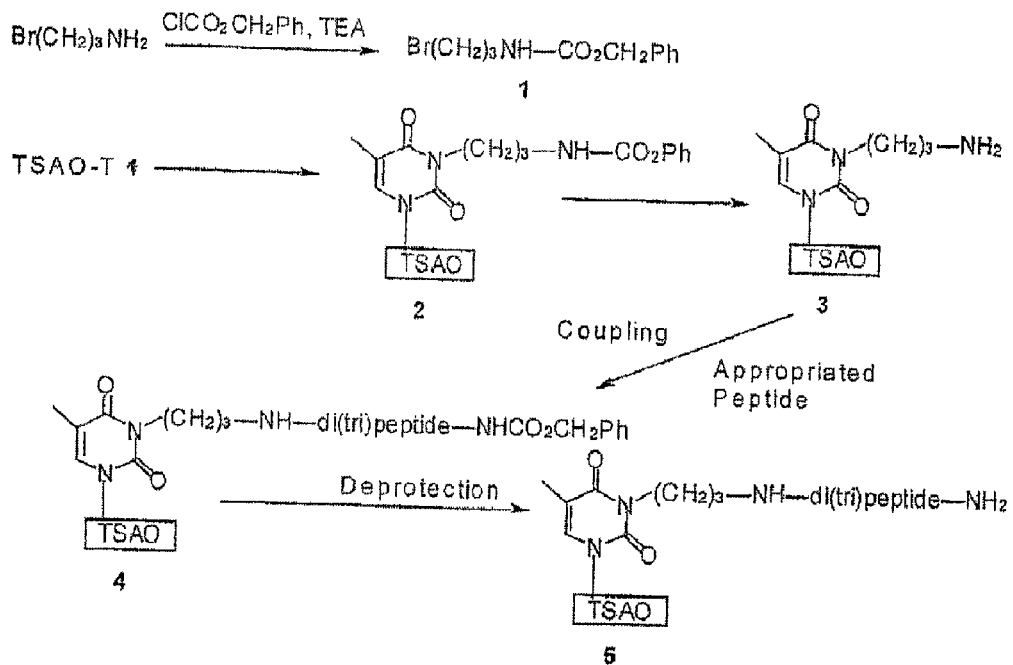
FIG. 8 presents an overview of the synthesis scheme used for the synthesis of TSAO derivatives.
Figure 9:
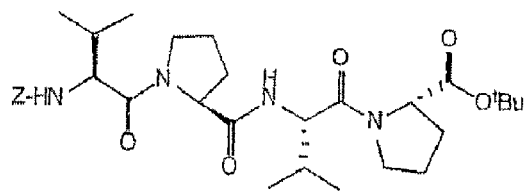
FIG. 9 shows precursor structures to prepare the tetrapeptide prodrug and structures of blocked and free dipeptide and tetrapeptide derivatives of different drugs.
Figure 9:
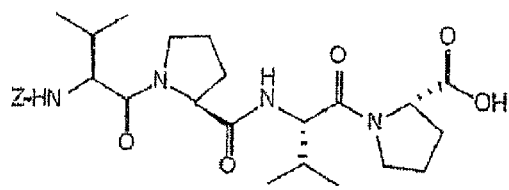
Figure 9:
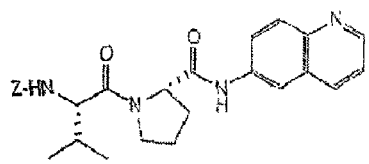
Figure 9:
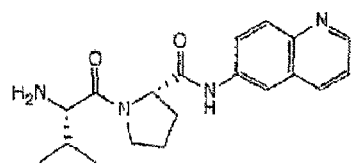
Figure 9:
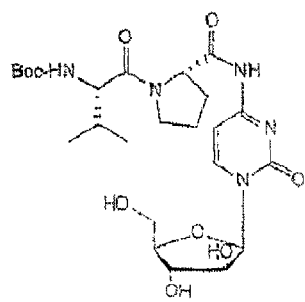
Figure 9:
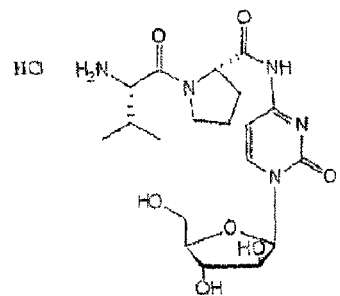
Figure 9:
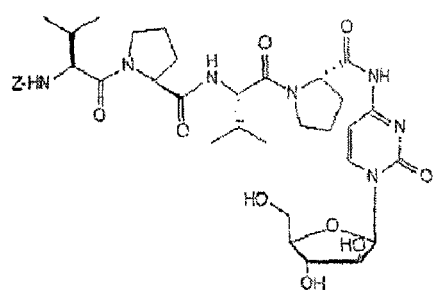
Figure 9:
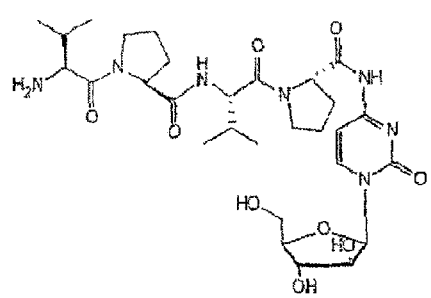
Figure 9:
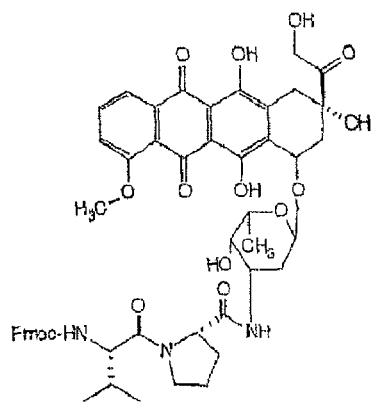
Figure 9:
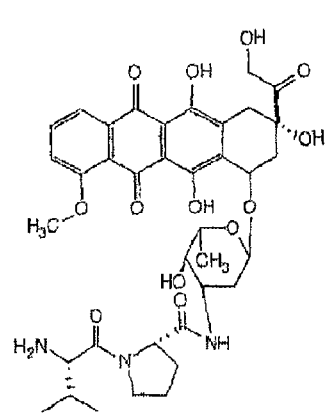

Interestingly, when the dipeptide-NAP-TSAO compounds were exposed to 20% human serum (diluted in PBS), the compounds were converted to one or two derivatives depending on the nature of the dipeptide (FIG. 6). For example, Val-Gly-NAP-TSAO was efficiently (but solely) converted to Gly-NAP-TSAO. Val-Leu-NAP-TSAO and Val-Phe-NAP-TSAO did convert to a limited extent to Leu-NAP-TSAO and Phe-NAP-TSAO, respectively, but also to NAP-TSAO. Interestingly, the Val-D-Pro-TSAO-NAP derivative that contains a penultimate proline residue in D-configuration, is very stable in the human serum. Only a very limited amount of NAP-TSAO (but not D-Pro-NAP-TSAO) had been detected (FIG. 6). The tripeptide derivative Val-Pro-Val-NAP-TSAO was very efficiently converted predominantly to Val-TSAO by human serum as also occurred in the presence of purified CD26 (data not shown).

Example 7

Solubility

Lipophilicity of a drug may strongly determine its solubility, plasma protein binding but also its ability to cross the blood-brain barrier. Different dipeptides or tetrapeptides linked to NAP-TSAO markedly influence the calculated log P values of the molecules (Table 3).

It is also clear that the nature of the dipeptide moiety present on NAP-TSAO markedly affect prodrug solubility in water. For example, only little amounts of prodrug appears in the water phase when Val-Ala had been linked to NAP-TSAO, whereas Val-Gly and particularly Val-Pro-linked to NAP-TSAO, had markedly increased water solubility (Table 4)

TABLE 3 calculated log p values of test compounds

| Compound | log Pa |
|---|---|
| 1. m-3T-TSAO | 3.21 |
| 2. NAP-TSAO | 2.38 |
| 3. Val-Pro-NAP-TSAO | 3.08 |
| 4. Val-OH-Pro-NAP-TSAO | 2.19 |
| 5. Val-Ala-NAP-TSAOI | 2.41 |
| 6. Ser-Pro-NAP-TSAO | 1.25 |
| 7. Lys-Pro-NAP-TSAO | 1.85 |
| 8. Asp-Pro-NAP-TSAO | 0.59 |
| 9. Asn-Pro-NAP-TSAO | 1.00 |
| Val-Pro-Lys-Pro-NAP-TSAO [SEQ ID no: 10] | 2.93 |
| Val-Pro-Asp-Pro-NAP-TSAO [SEQ ID no: 11] | 0.64 |
| Val-Pro-Val-Pro-NAP-TSAO [SEQ ID no: 6] | 4.15 |

TABLE 4 solubility of test compounds after 2 × 10 sec sonication and 4 days shaking of 1 mg/ml compound in Milli-Q water at room temperature$^a$

| Compound | Solubility (HPLC) | Spectrum (~265 nm) | $R_t$ (min) |
|---|---|---|---|
| CAM-422 (Val-Gly-NAP-TSAO) | 1,120,567 | 1.886 | 28.5 |
| CAM-424 (Val-Ala-NAP-TSAO) | 229,432 | 0.650 | 28.8 |
| CAM-430 (Val-D-Pro-NAP-TSAO) | 6,174,671 | 3.220 | 31.4 |
| 3-methyl-TSAO-T | 0 | 0.100 | 22.6 |

$^a$After shaking: centrifugation 50 min 15,000 rpm → U.V. spectrum or filter (0.45µ) → quantification by HPLC analysis (acetonitrile/Na phosphate buffer + heptanesulfonic acid).

As a conclusion, dipeptidyl or tripeptidyl derivatives of the lipophilic TSAO nucleoside analogue were shown to be efficient substrates for purified CD26, as well as for soluble CD26 activity present in human and bovine serum.

Oligopeptide derivatives of highly lipophilic water-insoluble drugs can make these drugs markedly more water-soluble, less plasma protein binding and can also increase their oral bioavailability and blood-brain barrier penetration. In addition, this technology allows a more specific targeting of drugs to CD26-expressing cells.

Prodrugs of the Anticancer Drug Doxorubicin and of 6-Aminoquinoline

Example 8

Conversion of Val-Pro-doxorubicin to doxorubicin and Val-Pro-6-aminoquinoline to 6-aminoquinoline by Purified CD26 in Function of Time Val-Pro-Doxorubicin (CAM 469) containing the dipeptide Val-Pro, linked to the amino sugar of doxorubicin was very efficiently converted to doxorubicin by CD26. When blocked at the amino terminal by Fmoc (CAM 468), no conversion to the parent drug was found (Table 5).

Conversion of the fluorescent 6-aminoquinoline dipeptide (CAM 475) in which Val-Pro was linked to the 6-amino group on the aromatic ring of the parent compound occurred very efficiently and resulted virtually in a complete conversion within 1 hr to the parent 6-aminoquinoline derivative.

TABLE 5

Dipeptide prodrugs of doxorubicin and 6-aminoquinoline: conversion to their parent compounds by purified CD26 (1.5 mUnits)

| | | | % conversion | | |
|---|---|---|---|---|---|
| CAM-nr | Product | RT(min) | 1 h | 4 h | 24 h |
| 468 | Fmoc-Val-Pro-Doxorubicin | 31.49 | 0 | 0 | 0 |
| 469 | H-Val-Pro-Doxorubicin | 16.49 | 78 | 95 | 97 |
| 475 | H-Val-Pro-6-Aminoquinoline | 14.32 | 99 | 100 | 100 |

Example 9

Separation of Dipeptide Prodrugs of NAP-TSAO, doxorubicin and 6-aminoquinoline

Doxorubicin (Doxo), CAM 469 (Val-Pro-Doxo) and CAM 468 (Fmoc-Val-Pro-Doxo): 16.2, 16.4 and 31.58 min, respectively; 6-aminoquinoline (CAM 483) and Val-Pro-6-aminoquinoline (CAM 475): 12.2 and 14.26 min, respectively. Lys-Pro-Asp-Pro-NAP-TSAO [SEQ ID NO: 8] (CAM 477), Asp-Pro-NAP-TSAO (CAM 435), NAP-TSAO (CAM 212): 22.8, 25.4 and 29.7 min, respectively.

Example 10

Figure 10:
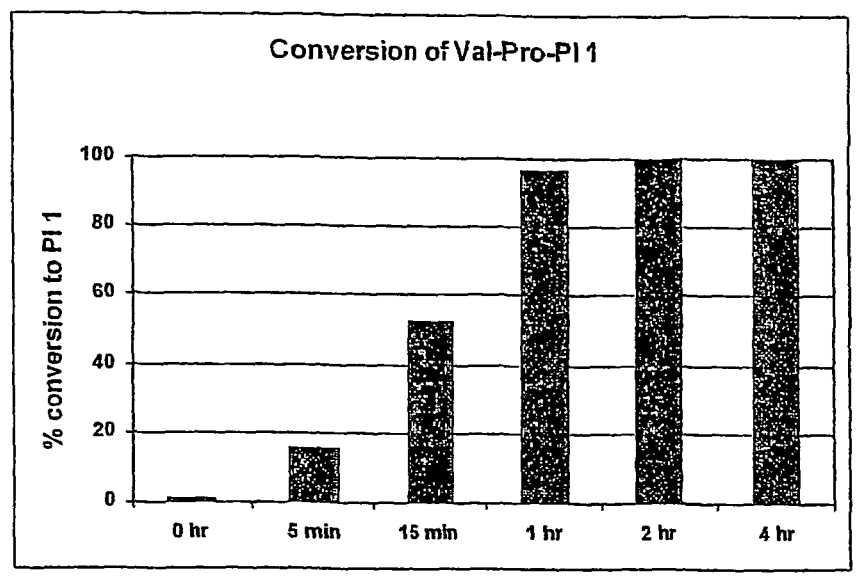
FIG. 10 shows the conversion of Val-Pro-PI 1 prodrug to PI 1 (protease inhibitor) in function of time. A: CD26; B: bovine serum; C: human serum (both 10% in PBS).
Figure 10:
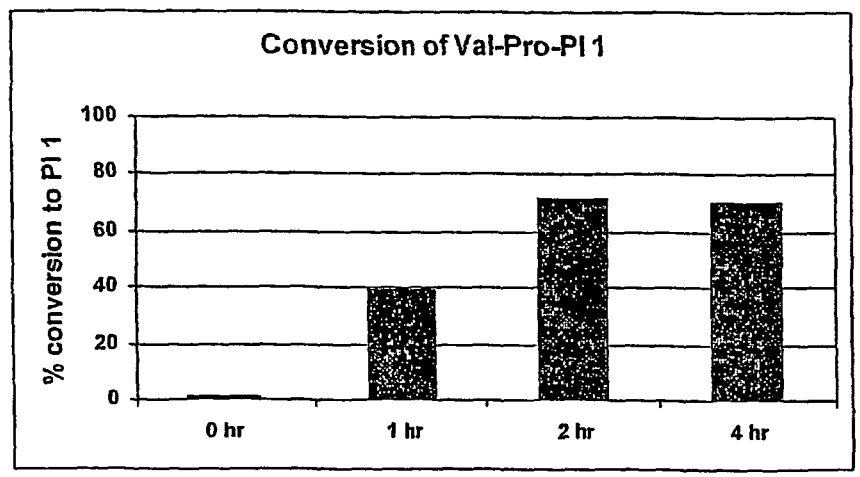
Figure 10:
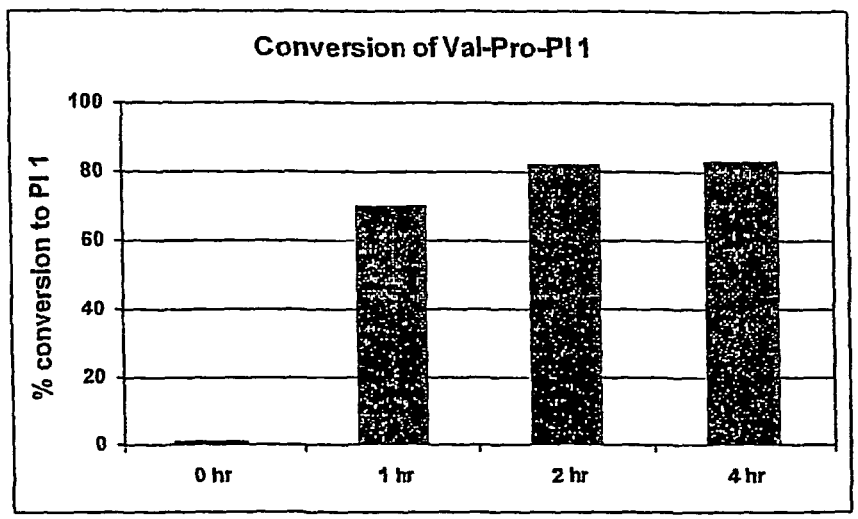
Figure 11:
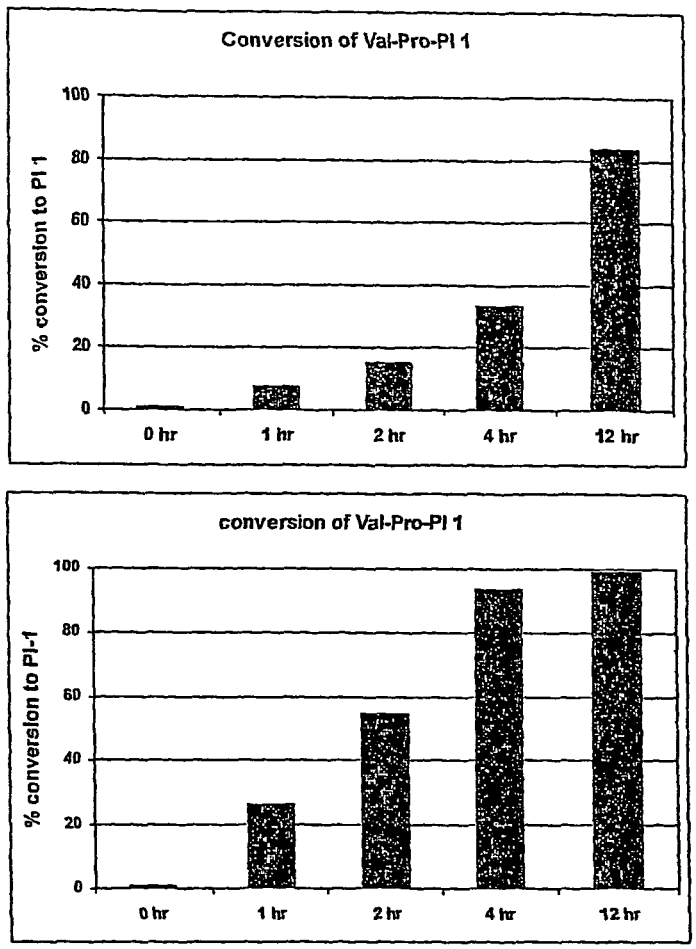
FIG. 11 shows the conversion of Val Pro-PI 1 prodrug to PI 1 (protease inhibitor) in function of time. Upper panel: Bovine serum (2% in PBS), Lower panel: Human serum (2% in PBS)

Conversion of PI-1 dipeptide (PI-2) to PI-1 by purified CD26, Human and Bovine Serum The dipeptide (Val-Pro) derivative of PI-1 (PI-2) was exposed to purified CD26 (FIG. 10), and 10% or 2% human or bovine serum, diluted in PBS (phosphate-buffered saline) (FIGS. 10 and 11). PI-2 was efficiently converted to PI-1 in all conditions tested. Within 60 min, PI-2 was completely converted to PI-1 by purified CD26. Ten percent BS or HS converted 40 to 70% of PI-2 to PI-1 in one hour (FIG. 10). Two percent BS and HS converted PI-2 to PI-1 by 8% and 25%, respectively. After 4 hrs, 35% and 95% of compound was hydrolyzed by BS and HS, respectively (FIG. 11).

Figure 12:
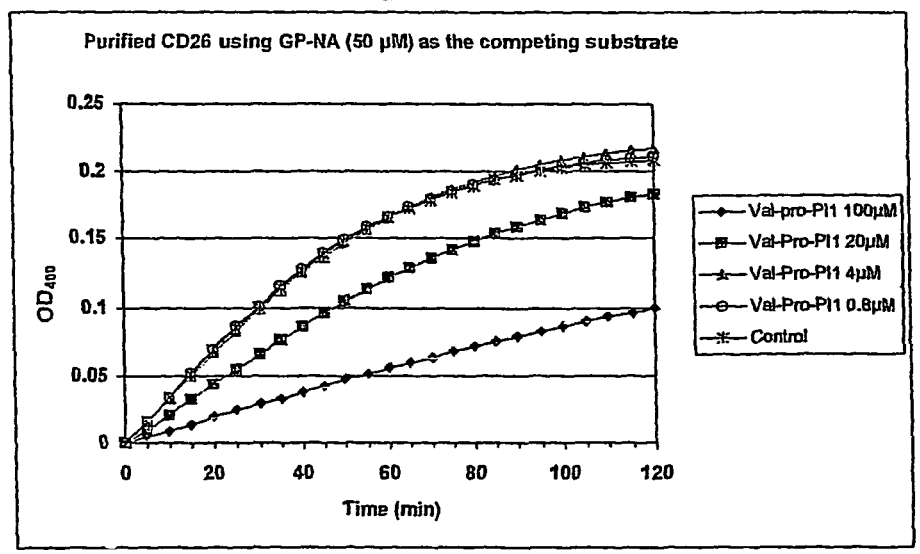
FIG. 12 shows the inhibitory (competitive) effect of Val-Pro-PI 1 on CD26-catalysed conversion of GP-pNa to GP+pNA (yellow).
Figure 13:
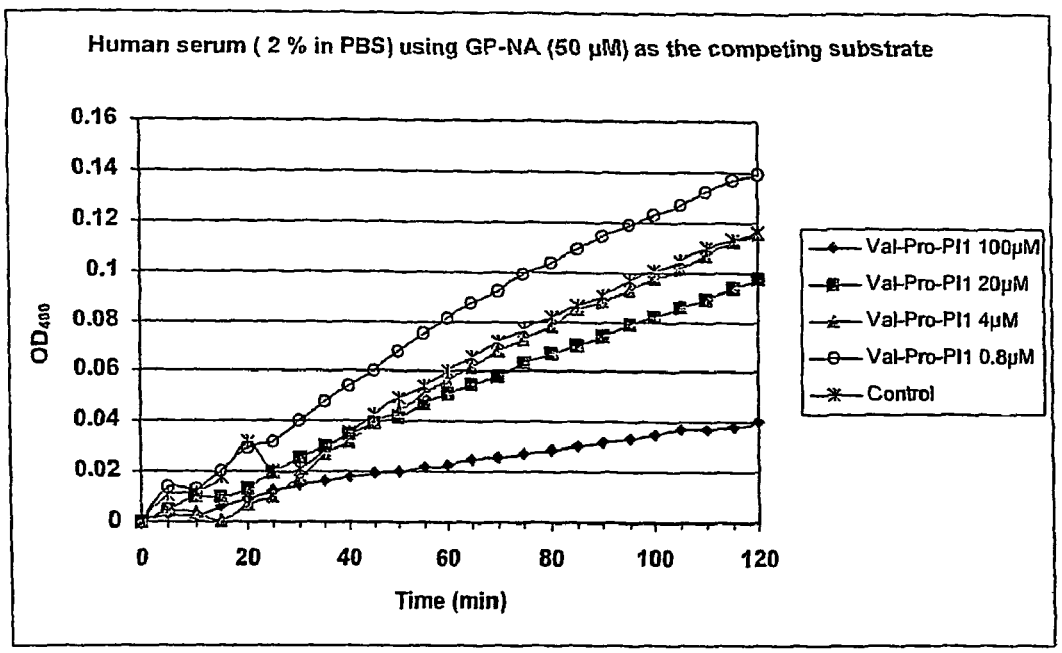
FIG. 13. Inhibitory (competitive) effect of Val-Pro-PI 1 on CD26-catalysed conversion of GPpNA to GP+pNA (yellow) in 2% human serum (in PBS).
Figure 14:
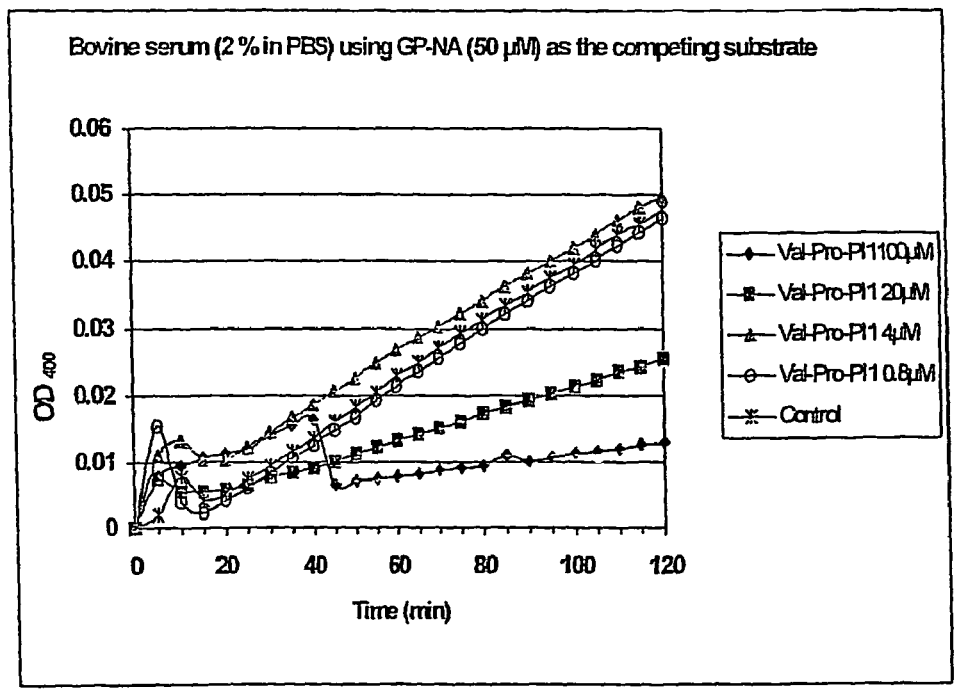
FIG. 14. Inhibitory (competitive) effect of Val-Pro-PI 1 on CD26-catalysed conversion of GPpNA to GP+pNA (yellow) in 2% bovine serum (in PBS).

In the presence of 50 µM GP-pNA (glycylprolyl-para-nitroanilide), 100 µM PI-2 efficiently competed with the substrate for CD26 (FIG. 12). Also 20 µM PI-2 could inhibit the release of pNA from GP-pNA, presumably by competitive inhibition of the CD26-catalysed reaction. Conversion of GP-pNA to pNA by two percent BS in PBS was even more efficiently inhibited by PI-2 than purified CD26 (FIG. 13). Also HS (2% in PBS)-catalysed GP-pNA conversion to pNA was competitively inhibited by PI-2 (FIG. 14).

Example 11

Separation PI-2 and PI-1 Compounds

Compounds were separated on a Reverse Phase RP-8 (Merck) using a gradient with buffer A (50 mM $NaH_2PO_4$+5 mM heptane sulfonic acid pH 3.2) and buffer B (acetonitrile). 0→2 min: 2% buffer B; 2→8 min: 20% buffer B; 8→10 min: 25% buffer B; 10→12 min: 35% buffer B; 12→30 min: 50% buffer B; 30→35 min: 50% buffer B; 35→40 min: 2% buffer B; 40→45 min: 2% buffer B. Flow rate: 1 ml/min. Rt values of PI-2 and PI-1 were 18.7 and 17.7 min, respectively.

General Methodology

Example 12

Compounds, Enzymes and Cells

The TSAO derivatives depicted in FIG. 1 can be synthesised as described below. GlyPro-pNA (GP-pNA), Diprotin A and Val-Pro were purchased from Sigma-Aldrich (Bornem, Belgium). CD26 was purified as described before [De Meester et al. *J. Immunol. Methods* (1996), 189: 99-105]. Foetal bovine serum (FBS) was obtained from Integro (Dieren, The Netherlands). Human serum represented a pooled serum that was derived from 10 healthy volunteers (blood donors). Human lymphocyte CEM cells were derived from the ATCC (Rockville, Md.).

Example 13

Preparation of Prodrugs General Procedure for the Synthesis of TSAO-Peptides-Z Protected (4)

A solution of the corresponding peptide (1.5 equiv.) (prepared following usual coupling method in peptide synthesis) in dichloromethane (2 mL), was successively treated, at room temperature, with (benzotriazol-1-yl-oxy)-tris-(dimethylamino)-phosphoniun hexafluorophosphate (BOP) (1.5 equiv.), amino-propyl TSAO derivative (NAP-TSAO) 3 (1 equiv.) and triethylamine (1.5 equiv.). The reaction mixture was stirred until complete disappearance of the starting compound (3) (10-12 hours). Then, the solvent was evaporated to dryness and the residue was dissolved in dry dichloromethane (2 mL), washed with 10% aqueous citric acid (10 mL), 10% aqueous NaHCO₃ (10 mL) and brine (2×10 mL). The organic layer was dried (Na₂SO₄) and evaporated to dryness. The residue was purified by CCTLC on the Chromatotron using dichloromethane: methanol (70:1) as the eluent to give dipeptide-NAP-TSAO compounds (4) (50-55% yield)
General Procedure for the Synthesis of Deprotected Peptide-TSAO Compounds (5)

A solution of the corresponding TSAO-NAP-peptides-Z-protected (4) (1 equiv.) in methanol containing Pd/C (10%) (40% wt/wt) was hydrogenated at 25 psi at room temperature for 2 h. The reaction mixture was filtered, and the filtrate was evaporated to dryness, under reduced pressure to give 5 (90% yield) as a foam.
General Peptide Chemistry Coupling of natural amino acids in order to form a peptide is straightforward for a person skilled in the art. Several chemical strategies are available of which the Fmoc and Boc chemistry are the most widely used. Fields G. B. gives an extensive description of the peptide chemistry that can be applied to couple amino acids to each other or to a therapeutic compound D [Fields in *Methods in Molecular Biology*, Vol. 35: Peptide Synthesis Protocols Humana Press Inc.: Totawa, (1994), pp. 17-27]. Solid phase as well as solution phase chemistry can be applied [Atherton & Sheppard Solid Phase Peptide Synthesis IRL Press: Oxford-New York-Tokyo, (1989)]. Protection strategies whereby functionalities of a therapeutic compound that can not react during the prodrug preparation procedures are blokked through coupling of a protecting group, will have to be used.

N-benzoyloxycarbonyl-3-bromo-propylamine (1)

To an ice cooled suspension of 3-bromopropylamine bromhydrate (0.9 g, 4.11 mmol) and triethylamine (1.3 mL, 9.05 mmol) in dry dichloromethane was slowly added a solution of benzyl chloroformiate (0.6 mL, 4.11 mmol) in dry dichloromethane (1 mL). The reaction mixture was stirred at room temperature overnight. Then it was washed with saturated aqueous NaCl (2×15 mL), dryed (anhidrous Na₂SO₄), filtered and evaporated to dryness. The residue was purified by CCTLC on the chromatotron using hexane, ethyl acetate (4:1), to give 0.8 g (72%) of (1) as a white foam.

[1-[2',5'-Bis-O-(tert-butyldimethylsilyl)-β-D-ribofuranosyl]-3-N-(3-(benzyl oxicarbonylmethyl)aminopropyl)thymine]-3'-spiro-5"-(4"-amino-1",2"-oxathiole 2",2"-dioxide) (2)

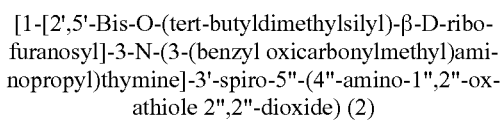

To a solution of TSAO-T (1 equiv.) in dry acetone (20 mL) was added dry K₂CO₃ (1.1 equiv.) and compound 1 (2 equiv.). The reaction mixture was refluxed for 6 h, and then, concentrated to dryness. The residue was dissolved in ethyl acetate (20 mL), washed with brine (2×20 mL), dried (Na₂SO₄), filtered and evaporated to dryness. The residue thus obtained was purified by flash column chromatography, using dichloromethane:methanol (70:1) as the eluent to give 2 (85%) as a white foam.

[1-[2',5'-Bis-O-(tert-butyldimethylsilyl)-β-D-ribofuranosyl]-3-N-(3-aminopropyl)thymine]-3'-spiro-5"-(4"-amino-1",2"-oxathiole-2",2"-dioxide) (3)

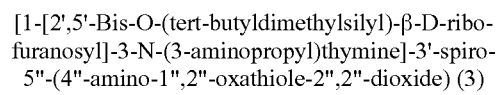

A solution of compound 2 (1 equiv.) in methanol containing Pd/C (10%) (30 wt %) was hydrogenated at 25 psi at room temperature for 2 h. The reaction mixture was filtered, and the filtrate was evaporated to dryness, under reduced pressure to give compound 3 (90%).
Boc-Val-Pro-Ara-C (A)

A solution of Boc-Val-Pro-OH (94.5 mg, 0.30 mmol) in dimethylformamide (1.5 mL), was successively treated, at room temperature, with 1-hydroxibenzotriazol (40.5 mg, 0.30 mmol), N,N-diisopropylcarbodiimide (46.7 µL, 0.30 mmol) and Ara-C (60.9 mg, 0.25 mmol). The stirring was continued until complete disappearance of the starting material (overnight stirring). Then, the solvent was evaporated, the residue was dissolved in ethyl acetate and washed with citric acid (10%), NaHCO₃ (10%) and brine. The organic layer was dried (Na₂SO₄) and evaporated to give a residue that was purified by CCTLC on the chromatotron with dichloromethane:methanol (20:1) to yield Ara-C-dipeptide (A) (21% yield)
HCl.H-Val-Pro-Ara-C (B)

Boc-Val-Pro-AraC (24.8 mg, 0.04 mmol) was treated with a 3.2 M solution of HCl in ethyl acetate (530 µL), the reaction was stirred at room temperature until complete disappearance of the starting material (30 minutes). Then, the solvent was evaporated to dryness, under reduced pressure to give B (80% yield).
Z-Val-Pro-Val-Pro-Ara-C [SEQ ID NO:9] (D)

A solution of Z-Val-Pro-Val-Pro-OH [SEQ ID NO:9] (134.4 mg, 0.24 mmol) in dimethylformamide (1.5 mL), was successively treated at room temperature with 1-hydroxibenzotriazol (33.3 mg, 0.24 mmol), N,N'-diisopropylcarbodiimide (38.4 µL, 0.24 mmol) and Ara-C (50 mg, 0.20 mmol). The stirring was continued until complete disappearance of the starting material (overnight). Then, the solvent was evaporated, and the residue was dissolved in ethyl acetate and washed with citric acid (10%), NaHCO₃ (10%) and brine. The organic layer was dried (Na₂SO₄) and evaporated to dryness leaving a residue that was purified by CCTLC on the chromatotron with dichloromethane:methanol (20:1) to give D (22% yield)

H-Val-Pro-Val-Pro-Ara-C (SEQ ID NO:6] (E)

A solution of the corresponding Ara-C-tetrapeptide-Z-protected (D) (24.7 mg, 0.03 mmol) in methanol containing Pd/C (10% wt/wt) (11.5 mg) was hydrogenated at 25 psi at room temperature for 2 h. The reaction mixture was filtered, and the filtrate was evaporated to dryness, under reduced pressure, to give D (90% yield).

Fmoc-Val-Pro-doxorubicin (F)

A solution of Fmoc-Val-Pro-OH and doxorubicin. HCl (50 mg, 0.08 mmol) in DMSO (4 mL), was successively treated at room temperature with N-[(dimethylamino)1H-1,2,3-triazolo[4,5-b]pyridino-1-ylmethylene]-N-methylmethanaminium hexafluorophosphate N-oxide (HATU) (36.0 mg, 0.09 mmol) and diisopropylethylamine (DIEA) (29.5 µL, 0.17 mmol). The reaction mixture was stirred at room temperature overnight. Then, the solvent was lyophilized and the residue was dissolved in ethyl acetate and washed with citric acid (10%), NaHCO$_3$ (10%) and brine. The organic layer was dried (Na$_2$SO$_4$) and evaporated to dryness to give F (45% yield).

H-Val-Pro-doxorubicin (G)

A solution of piperidine in dimethylformamide 50% (1.92 mL) was added to Fmoc-Val-Pro-doxorubicin (F) (29.7 mg, 0.03 mmol) and the reaction mixture was stirred at room temperature for 1 minute (the reaction colour changes form red to purple). Then, the reaction mixture was evaporated to dryness under reduced pressure and the residue thus obtained was purified by reverse phase chromatography with water/acetonitrile (70:1) to give the deprotected compound G (50% yield)

Z-Val-Pro-6-aminoquinoline (H)

A solution of Z-Val-Pro-OH (217.4 mg, 0.62 mmol) in dichloromethane (1.5 mL), was successively treated at room temperature. with 1-hydroxibenzotriazol (84.3 mg, 0.62 mmol), N,N'-diisopropylcarbodiimide (97.2 µL, 0.62 mmol) and 6-aminoquinoline (75 mg, 0.52 mmol). The stirring was continued until the complete disappearance of the starting material (overnight). Then, the solvent was evaporated, the residue was dissolved in ethyl acetate and washed with citric acid (10%), NaHCO$_3$ (10%) and brine. The organic layer was dried (Na$_2$SO$_4$) and evaporated leaving a residue that was purified by CCTLC on the chromatotron with hexane/ethyl acetate (1:4) to yield H (20 yield H-Val-Pro-6-aminoquinoline (I)

A solution of the corresponding Z-protected-dipeptide-6-Aminoquinoleine (H) (25.8 mg, 0.05 mmol) in methanol (4 mL) containing Pd/C (10% wt/wt) (10.5 mg) was hydrogenated at 25 psi at room temperature for 2 h. The reaction mixture was filtered, and the filtrate was evaporated to dryness, under reduced pressure to give 1 (90% yield).

Z-Val-Pro-Val-Pro-O$^t$Bu (X) [SEQ ID no: 9]

A solution of Z-Val-Pro-OH (681.3 mg, 1.95 mmol) in dichloromethane (6 mL), was successively treated at room temperature. with (benzotriazol-1-yloxy)tris(dimethylamino)phosphoniun hexafluorophale (BOP) (865.1 mg, 1.95 mmol), H-Val-Pro-O$^t$Bu.HCl (500 mg, 1.63 mmol) and triethylamine (TEA) (500 µL, 3.58 mmol). The mixture was stirred overnight at room temperature. Then, the solvent was evaporated, the residue was dissolved in dichloromethane and washed with citric acid (10%), NaHCO$_3$ (10%) and brine. The organic layer was dried (Na$_2$SO$_4$) and evaporated to dryness leaving a residue that was purified on a column chromatography with hexane-ethyl acetate, 2:1 to give X (68% yield).

Z-Val-Pro-Val-Pro-OH (Y) [SEQ ID no: 9]

A solution of Z-Val-Pro-Val-Pro-O$^t$Bu [SEQ ID No: 9] (1.1 mmol) was treated with trifluoroacetic acid (2.76 mL, 3.58 mmol) in dichloromethane (4.85 mL), the reaction was stirred at room temperature for 3 h. Then, the solution was evaporated to dryness and the residue was lyophilized to give Y (84% yield).

Example 14

Evaluation of the Inhibitory Effect of CD26 Inhibitors on the Conversion of Pro-Val-NAP-TSAO to NAP-TSAO by Purified CD26, Human Serum and Bovine Serum All enzyme activity assays were performed in Eppendorf tubes on a heating block at 37° C. To each tube were added 32 µl CD26 (at a final concentration of 1.5 milliUnits) or 10 µl foetal bovine serum (BS) (final concentration: 2.5% BS in PBS; preheated at 56° C. for 30 min) or 10 µl human serum (HS) (final concentration: 2.5% HS in PBS), 40 µl of appropriate concentrations of inhibitor (Diprotin A) solution in PBS (for the exact concentrations, see the legend to FIG. 5), CAM-405 (the substrate of the reaction) at 500M (final concentration) and PBS to reach a total volume of 400 µl. The pH of the reaction mixture was 7.5, which is virtually identical to the physiological pH of plasma. The reaction was started by the addition of the enzyme or serum and carried out at 37° C. After 5 hr, 100 µl reaction mixture was taken from the Eppendorf tube and added to 200 µl cold methanol to precipitate the proteins. After 10 min standing on ice, the contents of the tubes were centrifuged and the supernatants analysed by HPLC on a reverse phase column (RP-8, Merck Laboratories). CAM-405 was separated from CAM-212 (the product of the reaction) by a gradient of 50 mM sodium phosphate+5 mM heptane sulfonic acid pH 3.2 (Buffer A) and acetonitrile (Buffer B) as follows: Buffer A: 98%+2% Buffer B, 2 min; linear gradient to 20% Buffer. B, from 2 to 8 min; linear gradient to 25% Buffer B from 8 to 10 min; linear gradient to 35% Buffer B from 10 to 12 min; linear gradient to 50% Buffer B from 12 to 30 min; 50% Buffer B from 30 to 35 min; linear gradient to 98% Buffer A+2% Buffer B from 35 to 40 min; 98% Buffer A from 40 to 45 min. The retention times of CAM-405 and CAM-212 were 29.3 and 30.0 min, respectively.

Example 15

Measuring the Solubility and Bioavailability of the Prodrugs

In first instance methods exist to predict the solubility of a compound. For example in J Chem Int Comput Sci 1998 May-June; 38 (3): 450-6 the aqueous solubility prediction of drugs based on molecular topology and neural network modeling has been described.

In fact, all parameters relevant for solubility and bioavalability (pKa, partition coefficient, etc.) can be determined. "Drug Bioavailability: Estimation of Solubility, Permeability, Absorption and Bioavailability" gives a comprehensive overview of these parameters and their determination or prediction (ISBN 352730438X).

Partition coefficients are a measurement of lipophilicity. Expressed numerically as 'log P' values, they are the ratios between the concentrations of substances in two immiscible phases, such as water/octanol or water/liposomes and they can be easily calculated. Substances with high log P values dissolve better in fats and oils than in water. This enhances their ability to enter lipid (fat-based) membranes in the body by passive diffusion, thereby enhancing their potential for absorption.

Many drugs have a log P value of between one and four, making them suitable for oral methods of delivery. Drugs with high log P are usually poorly soluble in water. They may be lipid-soluble, but they cannot dissolve in the GI tract, so can't diffuse into the gut wall. If they do enter membranes, they may become trapped, with resultant toxic effects.

The partition coefficient can also be calculated. A method for log P prediction developed at Molinspiration (miLog P1.2) is based on the group contributions. Group contributions have been obtained by fitting calculated log P with experimental logo for a training set of several thousands drug-like molecules. The method can be used by used at www.molinspiration.com/services/logp.html (QSAR 15,403 (1996)). Many other Log P determination programs are available.

Examples 16-20

Experimental Part for the Preparation of COMPOUNDS OF FORMULA (I)

The examples describing the preparation of prodrug compounds of formula (I) will be based on the HIV protease inhibitor having the formula

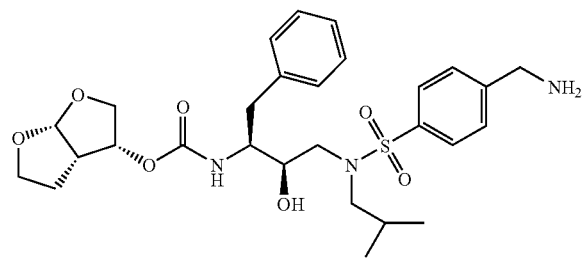

hereinafter referred to as PI 1

Example 16

Val-Pro-PI 1

Step1

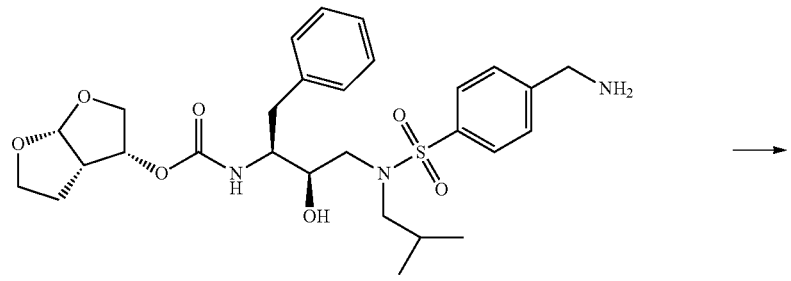

1.1

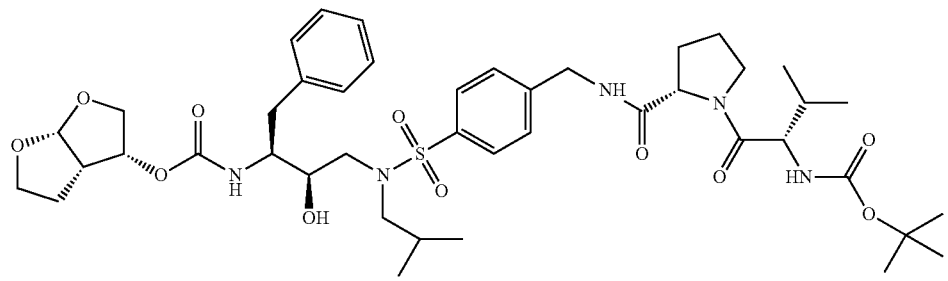

1.2

Compound 1.1 (0.95 g; 1.69 mmol) and Boc-Val-Pro-OH (0.53 g; 1.7 mmol) were dissolved in 10 ml N,N-dimethylformamide. EDCI (0.36 g; 1.9 mmol) and HOAt (0.023 g; 0.17 mmol) were added and stirred at room temperature for 20 hours. The reaction mixture was poured in H2O and extracted twice with ethylacetate. The combined organic layer was washed with brine and then dried over Na$_2$SO$_4$. Solvent was removed and the obtained crude product purified by column chromatography (eluent:ethylacetate). Compound 1.2 was obtained as a white solid (yield 55%, purity 95% LC-MS).

Step 2

To a solution of compound 1.2 (0.77 g; 09 mmol) in 10 ml CH$_2$Cl$_2$ was added 10 ml trifluoroacetic acid. After stirring the reaction mixture at room temperature for 3 hours, the solvent was removed. The crude mixture was purified by column chromatography yielding 0.42 g of compound 1.3 (yield 61%, purity 95% LC-MS)

Example 17

Asp-Pro-PI 1

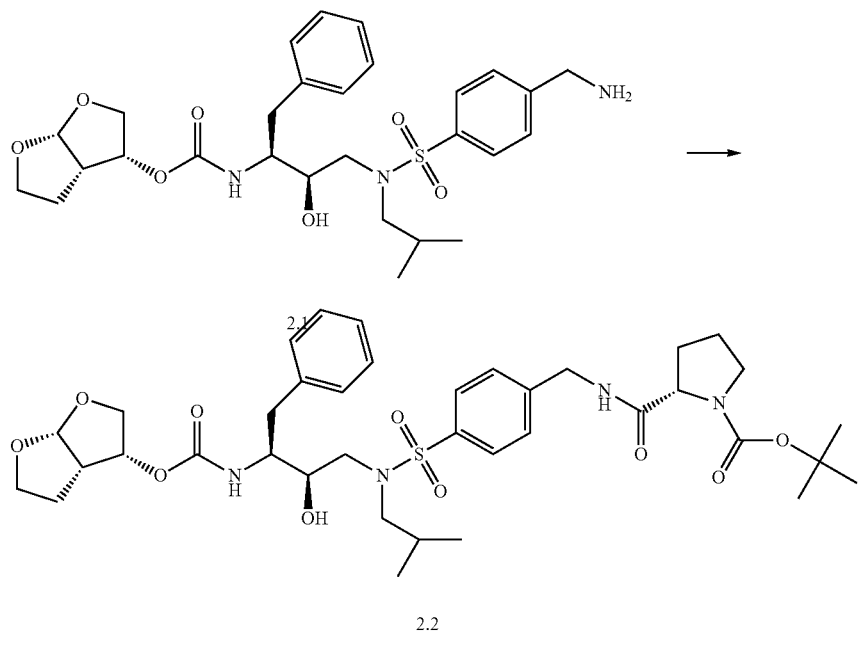

2.2

Compound 2.1 (3.16 g; 5.63 mmol) and Boc-Pro-OH (1.33 g; 6.18 mmol) were dissolved in 30 ml N,N-dimethylformamide. EDCI (1.18 g; 6.18 mmol) and HOAt (0.077 g; 0.5 mmol) were added and stirred for 36 hours. Ethylacetate and 0.1 N HCl were added and the resulting reaction mixture was extracted 3 times with ethylacetate. The combined organic layer was washed with 0.1 N HCl, H$_2$O, saturated NaHCO$_3$, water and brine. After drying over Na$_2$SO$_4$ and evaporation of the solvent a white foam (4.39 g, 103%) was obtained. After trituration in diisopropylether, 3.9 g of compound 2.2 was obtained (yield 93%, purity 97% LC-MS)

Step 2

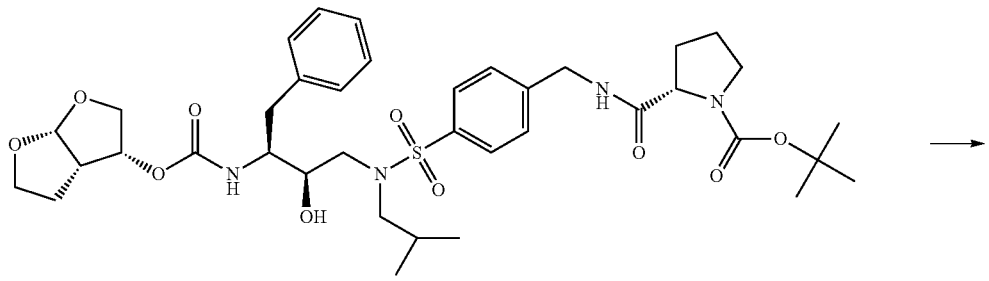

2.2

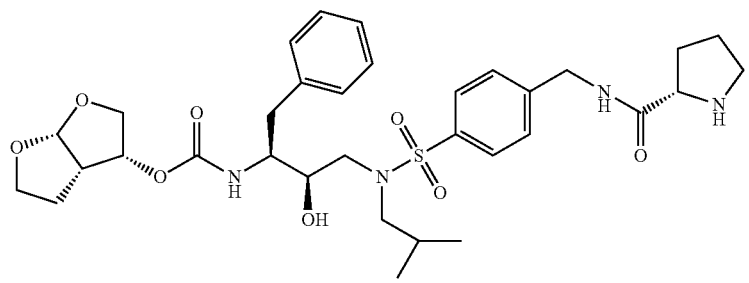

2.3

A mixture of compound 2.3 (3.7 g; 4.8 mmol) and 15 ml trifluoroacetic acid in 40 ml CH$_2$Cl$_2$ was stirred at room temperature for 2 hours. After evaporation of solvent the crude mixture was partitioned between ethylacetate and saturated NaHCO$_3$. The organic layer was separated, washed with brine and dried over Na$_2$SO$_4$. Re-slurry of the crude solid in diisopropylether and filtration yielded 2.73 g of compound 2.3 (yield 85%, purity>90% NMR).

Step 3

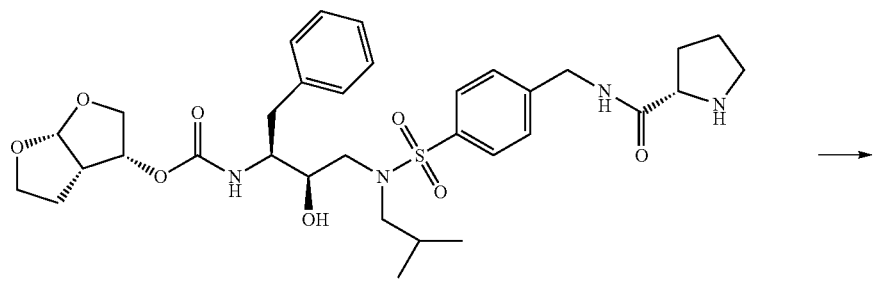

2.3

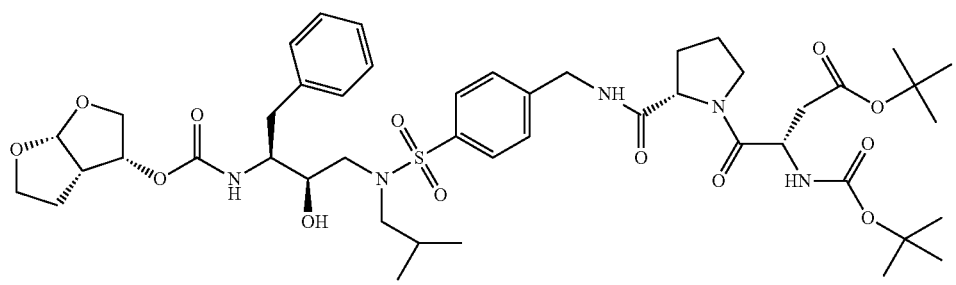

2.4

To a solution of compound 2.3 (1.0 g; 1.5 mmol) and Boc-Asp(OtBu)-OH (0.48 g; 1.7 mmol) in 30 ml N,N-dimethylformamide was added EDCI (0.32 g; 1.7 mmol) and HOAt (0.02 g; 0.15 mmol). After overnight stirring at room temperature the reaction mixture was partitioned between ethylacetate and 0.1 N HCl. The H₂O-layer was extracted 3 times and the combined organic layer was washed with 0.1N HCl, H₂O, saturated NaHCO₃ and H₂O. After drying over Na₂SO₄, the solvent was removed and the residue was triturated in diisopropylether. 1.12 g of compound 2.4 was obtained (yield 79%, purity 94% LC-MS)

Step 4

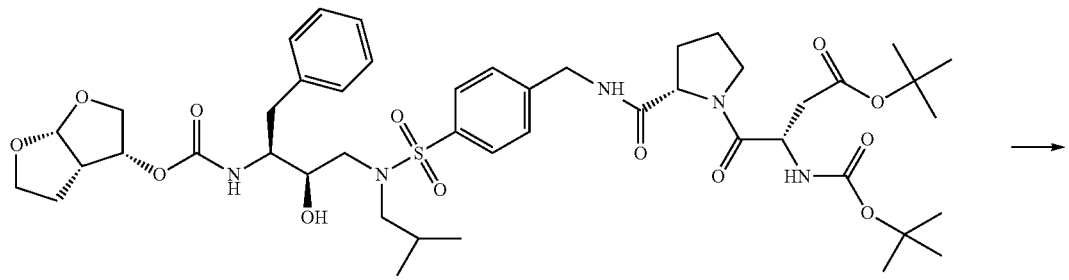

2.4

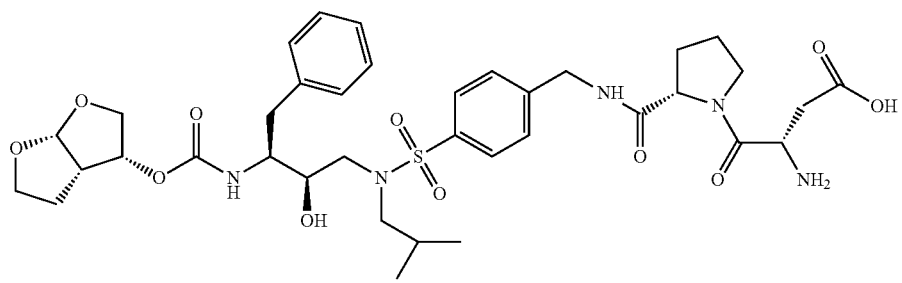

2.5

Deprotection of compound 2.4 to 2.5 was performed in an analogously to the procedure for deprotecting compound 2.2 to compound 2.3.

Example 18

Asp-Pro-Lys-Pro-PI 1 [SEQ ID NO: 5]

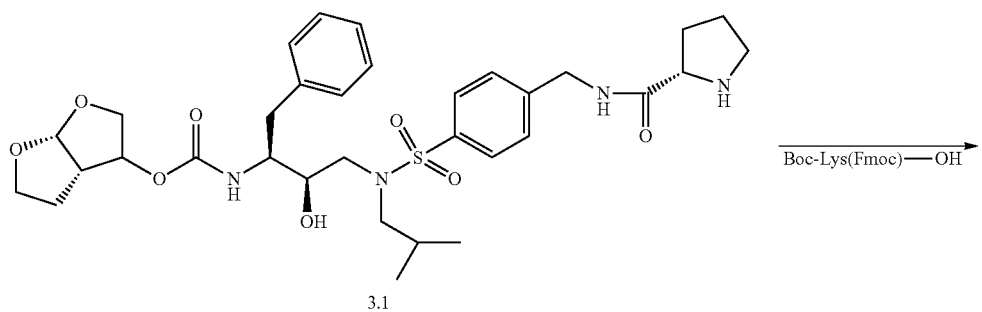

3.1

Boc-Lys(Fmoc)—OH

-continued
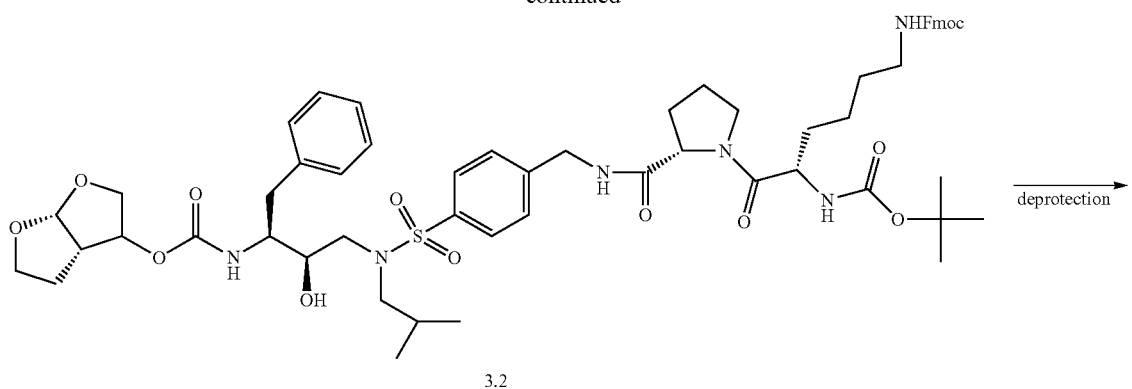
3.2 → deprotection
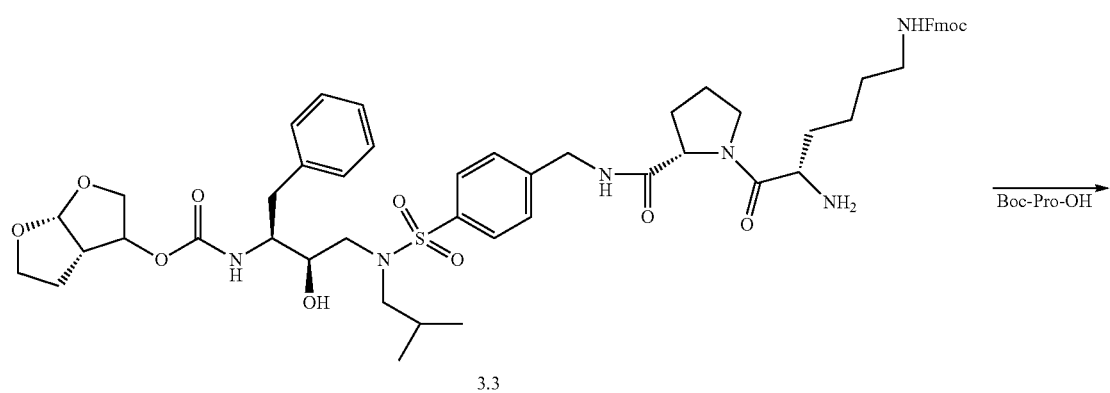
3.3 → Boc-Pro-OH
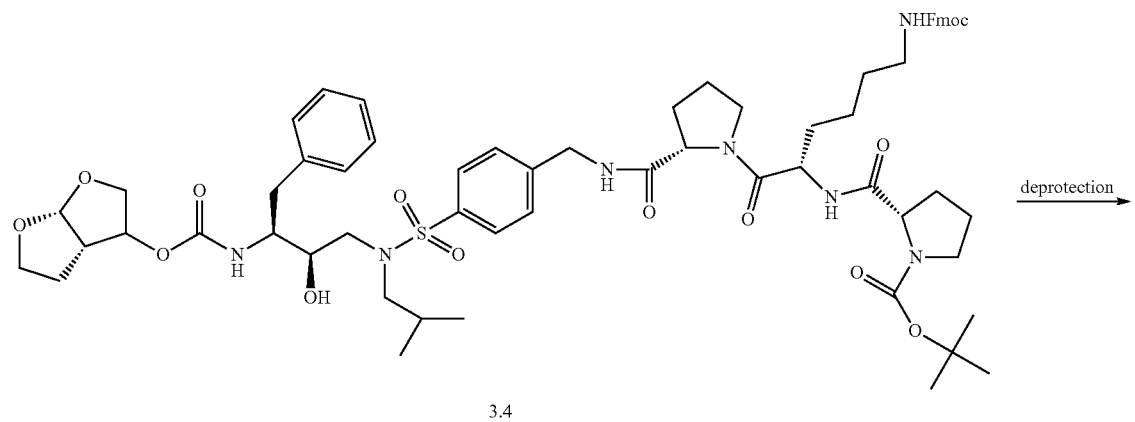
3.4 → deprotection
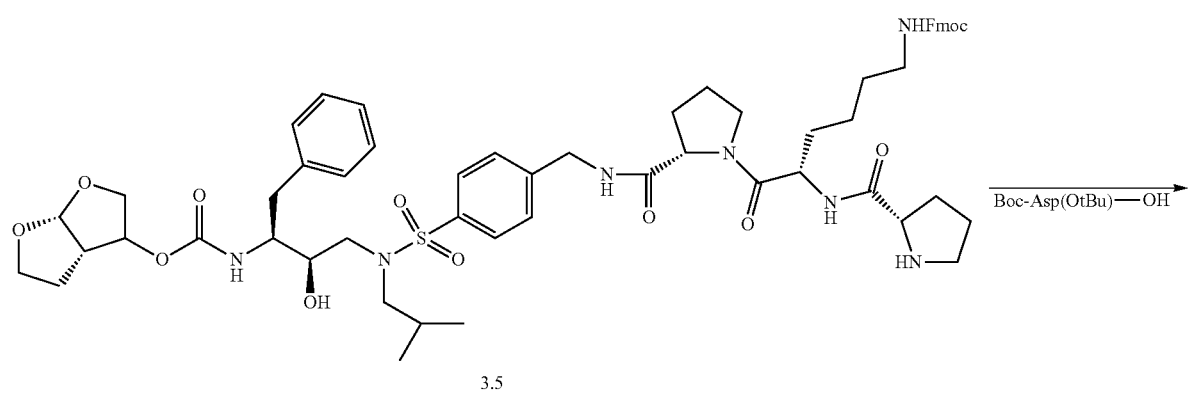
3.5 → Boc-Asp(OtBu)—OH

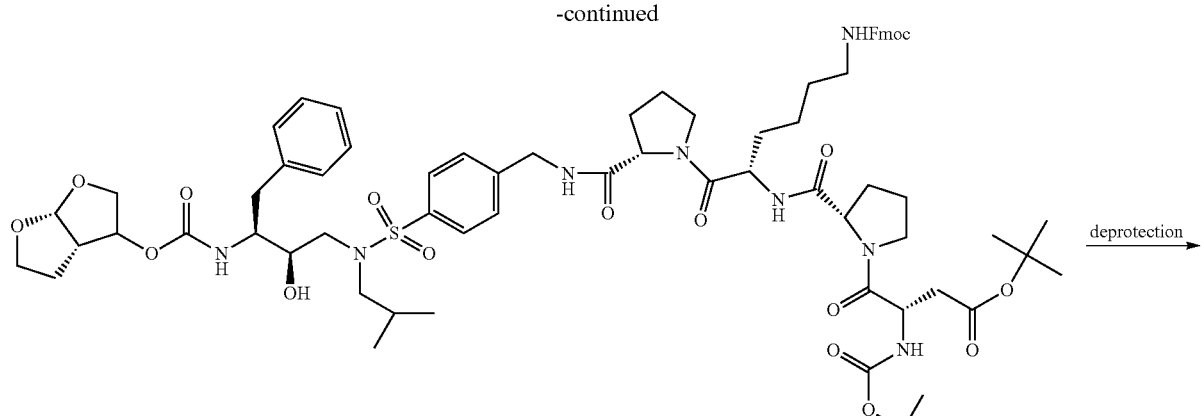

3.6

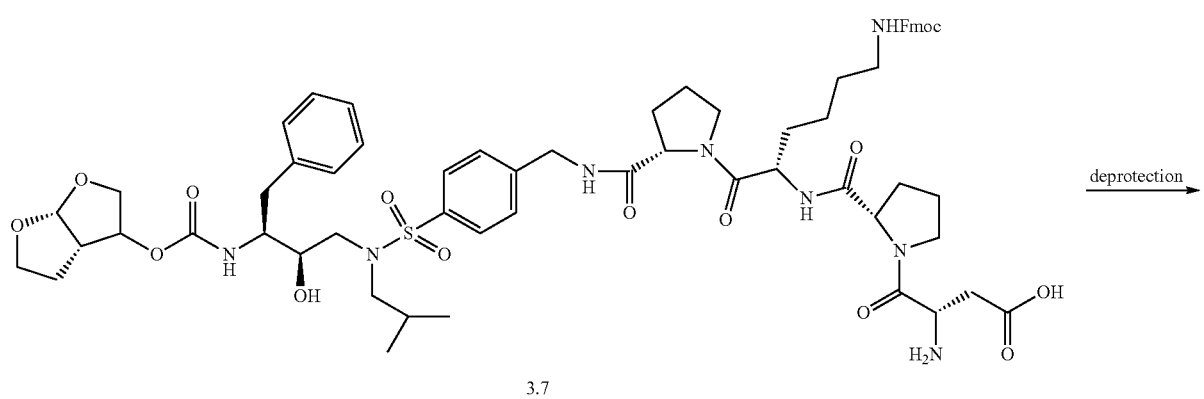

3.7

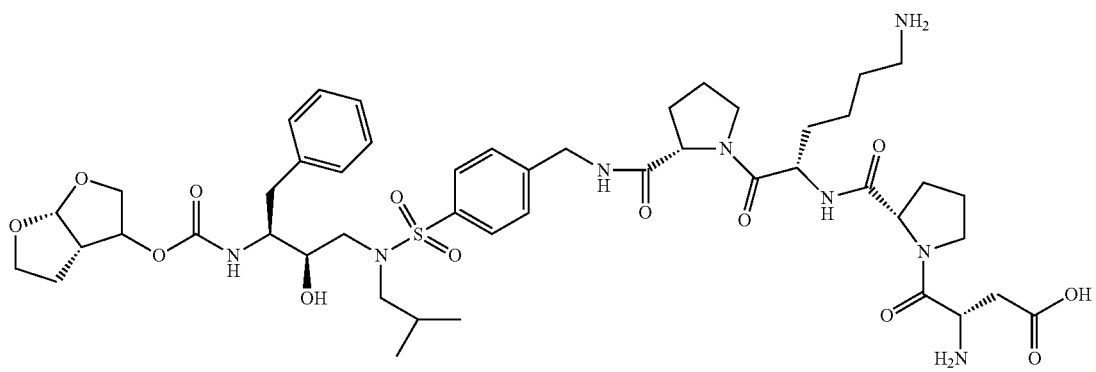

3.8

Using analogous reaction procedures as described in examples 1 and 2, Boc-Lys(Fmoc)-OH was coupled to compound 3.1 (as prepared in example 2), yielding compound 3.2. After Boc-deprotection, compound 3.3 was obtained. Boc-Pro-OH was then coupled to compound 3.3, yielding compound 3.4 which was subsequently Boc-deprotected thus yielding compound 3.5. Compound 3.5 was coupled with Boc-Asp(OtBu)-OH yielding compound 3.6 which was first Boc-deprotected and then Fmoc-deprotected using dimethylamine in tetrahydrofuran, thus yielding compound 3.8 corresponding to Asp-Pro-Lys-Pro-PI 1. [SEQ ID NO: 5]

Example 19

Conversion of Val-Pro-PI 1 to PI 1 by purified CD26, Human and Bovine Serum

The dipeptide (Val-Pro) derivative of PI 1 (Val-Pro-PI 1) was exposed to purified CD26 (FIG. 10), and 10% or 2% human or bovine serum, diluted in PBS (phosphate-buffered saline) (FIGS. 10 and 11). Val-Pro-PI 1 was efficiently converted to PI 1 in all conditions tested. Within 60 minutes, Val-Pro-PI 1 was completely converted to PI 1 by purified CD26. Ten percent BS or HS converted 40 to 70% of Val-Pro-PI 1 to PI 1 in one hour (FIG. 10). Two percent BS and HS converted Val-Pro-PI 1 to PI 1 by 8% and 25%, respectively. After 4 hrs, 35% and 95% of compound was hydrolyzed by BS and HS, respectively (FIG. 11). In the presence of 50 μM GP-pNA (glycylprolyl-para-nitroanilide), 100 μM Val-Pro-PI 1 efficiently competed with the substrate for CD26 (FIG. 12). Also 20 μM Val-Pro-PI 1 could inhibit the release of pNA from GP-pNA, presumably by competitive inhibition of the CD26-catalysed reaction. Conversion of GP-pNA to pNA by two percent BS in PBS was even more efficiently inhibited by Val-Pro-PI 1 than purified CD26 (FIG. 13). Also HS (2% in PBS)-catalysed GP-pNA conversion to pNA was competitively inhibited by Val-Pro-PI 1 (FIG. 14).

Example 20

Separation of Val-Pro-PI 1 and PI 1 Compounds

Compounds were separated on a Reverse Phase RP-8 (Merck) using a gradient with buffer A (50 mM $NaH_2PO_4$+5 mM heptane sulfonic acid pH 3.2) and buffer B (acetonitrile).

0→2 min: 2% buffer B; 2→8 min: 20% buffer B; 8→10 min: 25% buffer B; 10→12 min: 35% buffer B; 12→30 min: 50% buffer B; 30→35 min: 50% buffer B; 35→40 min: 2% buffer B; 40→45 min: 2% buffer B. Rt values of Val-Pro-PI 1 and PI 1 were 18.7 and 17.7 min, respectively.

Example 21

Acetyl-ACV[9-(2-acetoxyethoxymethyl)guanine] (1): A solution of acyclovir (96.8 mg, 0.43 mmol) in dimethylformamide (1.5 mL), was treated with acetic anhydride (122. 7 J-, 1.29 mmol) and 4-dimethylaminopirydine (DMAP) (5.3 mg, 0.04 mmol). The reaction mixture was stirred at room temperature for 18 hours. The solvent was evaporated to dryness to give 1 (91% yield)

Z-Val Pro-Cl (2): A solution of Z-Val-Pro-OH (228 mg, 0.65 mmol) in dichloromethane (4.5 mL), was treated with thionyl chloride (95 ZL, 1.30 mmol) and the reaction was stirred at room temperature for 2 hours. The solvent was evaporated to dryness to give pure compound 2 (quantitative yield)

Z-Val-Pro-ACV-OAc (3): A solution of 1 (50 mg, 0.87 mmol) in pyridine (1.0 mL), was treated with a solution of Z-Val-Pro-Cl (2) in dimethylformamide. The reaction was stirred until the complete disappearance of the starting material (2-3 days). The solvent was evaporated to dryness and the residue was dissolved in ethyl acetate (5 ml) and washed with citric acid (10%), NaHCO3 (10%) and brine. The organic layer was dried (Na2SO4) and evaporated to give a residue that was purified by CCTLC on the chromatotron with dichloromethane:methanol (20:1) to give 3 (39% yield)

H-Val-Pro-ACV-OAc (4): A solution of the Z-protected compound (3) (15.8 mg, 0.03 mmol) in methanol (5 mL) containing Pd/C (10% wt/wt) (10.2 mg) was hydrogenated at 35 psi at room temperature for 4 h. The reaction mixture was filtered, and the filtrate was evaporated to dryness, under reduced pressure, to give 4 (90% yield).

H-Val-Pro-ACV (5): A mixture of H-Val-Pro-ACV-OAc (4) (1 equiv) and 40% methyl amine aqueous solution (5 mL) was stirred at room temperature for 1 h. The solvent was removed in vacuo and the residue was purified by CCTLC on the chromatotron with dichloromethane:methanol (20:1 to give 5 (22% yield)

Reaction Scheme Representing the Synthesis of Acyclovir Prodrugs:

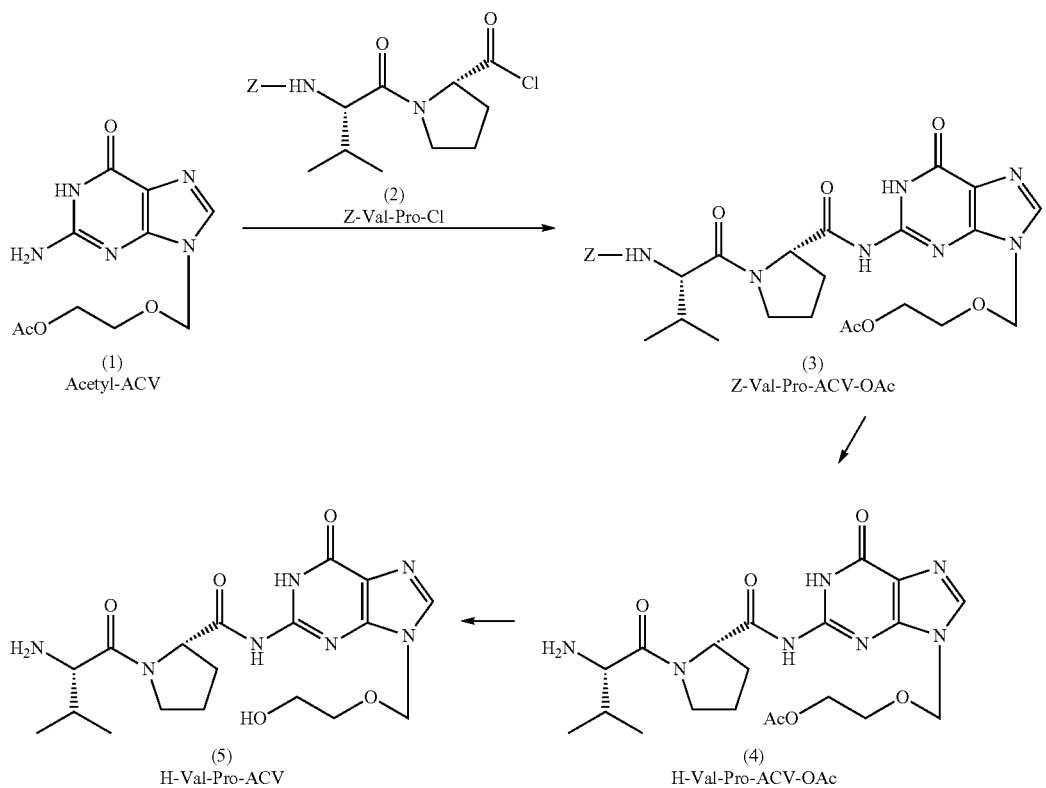

The invention claimed is:

1. A method of treatment of a patient having a viral infection, which comprises administering to said patient a prodrug comprising a therapeutic compound D linked to an oligopeptide having a general structure H—[X—Y]$_n$,
   wherein X is an amino acid, wherein n is selected from 1, 2, 3, 4 and 5; and
   wherein Y is an amino acid selected from the group consisting of proline, hydroxyproline, and dihydroxyproline; and
   wherein a binding via an amide occurs between said oligopeptide H-[X—Y]$_n$ and a linker on said therapeutic compound; and
   wherein said therapeutic compound D is an antiviral drug other than a drug with inhibitory activity on CD26/DPPIV enzymatic activity; and
   wherein said therapeutic compound D is not an amino acid, a peptide or a protein.

2. The method of claim 1, wherein n=2-5.

3. The method according to claim 1, wherein the oligopeptide having a general structure H—[X—Y]$_n$, is a tetrapeptide or hexapeptide, and wherein at least one X is a hydrophobic or aromatic amino acid.

4. The method according to claim 1, wherein the oligopeptide having a general structure H—[X—Y]$_n$, is a tetrapeptide or hexapeptide, and wherein at least one X is a neutral or acidic amino acid.

5. The method according to claim 1, wherein the oligopeptide having a general structure H—[X—Y]$_n$, is a tetrapeptide or hexapeptide, and wherein at least one X is a basic amino acid.

6. The method according to claim 1, wherein the oligopeptide having a general structure H—[X—Y]$_n$, is a tetrapeptide or hexapeptide selected from the group of Val-Y—[X—Y]$_{1-2}$.

7. The method according to claim 1, wherein the linker has a general structure of an oligopeptide A$_m$, wherein A is any amino acid, m is between 1 and 15, wherein A$_m$ is bound with its amino terminus to the carboxy terminus of H—[X—Y]$_n$ and wherein A$_m$ is bound with its carboxy terminus to said therapeutic compound D via an amide or ester binding.

8. The method according to claim 7, wherein m=1.

9. A method of treatment of a patient having a viral infection, which comprises administering to said patient a prodrug comprising a therapeutic compound TSAO linked to an oligopeptide having a general structure H—[X—Y]$_n$,
   wherein X is an amino acid,
   wherein n is selected from 1, 2, 3, 4 and 5,
   wherein Y is an amino acid selected from the group consisting of proline, alanine, hydroxyproline, dihydroxyproline, thiazolidinecarboxylic acid (thioproline), dehydroproline, pipecolic acid (L-homoproline), azetidinecarboxylic acid, aziridine carboxylic acid, glycine, serine, valine, leucine, isoleucine, and threonine, and
   wherein a binding between a carboxy terminus of H—[X—Y]$_n$ and an amino group of said therapeutic compound TSAO or an amino group of a linker on said therapeutic compound TSAO occurs via an amide.

10. The method of claim 9, wherein n=2-5.

11. The method according to claim 9, wherein the oligopeptide having a general structure H—[X—Y]$_n$, is a tetrapeptide or hexapeptide, and wherein at least one X is an hydrophobic or aromatic amino acid.

12. The method according to claim 9, wherein the oligopeptide having a general structure H—[X—Y]$_n$, is a tetrapeptide or hexapeptide, and wherein at least one X is a neutral or acidic amino acid.

13. The method according to claim 9, wherein the oligopeptide having a general structure H—[X—Y]$_n$, is a tetrapeptide or hexapeptide, and wherein at least one X is a basic amino acid.

14. The method according to claim 9, wherein the oligopeptide having a general structure H—[X—Y]$_n$, is a tetrapeptide or hexapeptide selected from the group of Val-Y—[X—Y]$_{1-2}$.

15. The method according to claim 9, wherein Y is proline, dihydroxyproline, hydroxyproline or alanine.

16. The method according to claim 9, wherein the linker has a general structure of an oligopeptide A$_m$, wherein A is any amino acid, m is between 1 and 15, wherein A$_m$ is bound with its amino terminus to the carboxy terminus of H—[X—Y]$_n$ and wherein A$_m$ is bound with its carboxy terminus to said therapeutic compound TSAO via an amide binding.

17. The method according to claim 16, wherein m=1.

* * * * *